(12) United States Patent
Reddy

(10) Patent No.: US 7,491,517 B2
(45) Date of Patent: Feb. 17, 2009

(54) **METHOD OF PRODUCING MENINGOCOCCAL MENINGITIS VACCINE FOR *NEISSERIA MENINGITIDIS* SEROTYPES A, C, Y, AND W-135**

(76) Inventor: Jeeri R Reddy, 6817 North 97th Cir., Omaha, NE (US) 68122

( * ) Notice: Subject to any disclaimer, the term of this patent is extended or adjusted under 35 U.S.C. 154(b) by 51 days.

(21) Appl. No.: 11/680,471

(22) Filed: Feb. 28, 2007

(65) Prior Publication Data

US 2008/0020428 A1 Jan. 24, 2008

Related U.S. Application Data

(60) Provisional application No. 60/831,682, filed on Jul. 19, 2006.

(51) Int. Cl.
| | |
|---|---|
| *C12P 19/00* | (2006.01) |
| *C12P 19/26* | (2006.01) |
| *C12P 19/04* | (2006.01) |
| *C12N 1/12* | (2006.01) |
| *C12N 1/20* | (2006.01) |
| *A61K 39/095* | (2006.01) |

(52) U.S. Cl. ............ 435/72; 435/84; 435/101; 435/252.1; 435/253.6; 424/250.1

(58) Field of Classification Search .......... None
See application file for complete search history.

(56) References Cited

U.S. PATENT DOCUMENTS

| | | | |
|---|---|---|---|
| 2,844,515 A * | 7/1958 | Sobotka et al. ........ 435/252.5 |
| 4,123,520 A | 10/1978 | Hagopian et al. | |
| 4,182,751 A | 1/1980 | Ayme | |
| 5,494,808 A | 2/1996 | Fu | |
| 6,642,017 B2 | 11/2003 | Weiser | |
| 6,933,137 B2 | 8/2005 | Egen et al. | |
| 2005/0002957 A1 | 1/2005 | Bordner | |
| 2006/0088554 A1 | 4/2006 | Ryall | |

FOREIGN PATENT DOCUMENTS

| | | |
|---|---|---|
| WO | WO03007985 | 1/2003 |
| WO | WO2005004909 | 1/2005 |

OTHER PUBLICATIONS

Atlas et al in Handbook of Microbiological Media 2nd edition, 1997, p. 1, p. 4-7.*
Clementi et al. Enzyme and Microbial Technology 17: 983-988, 1995.*
Duta et al. Electron. J. Biotechnol. V. 9 No. 4 Jul. 2006.*
Maccio et al Soil Biology and Biochemistry, Feb. 2002, vol. 34, No. 2, p. 201-208.*
Goebel et al J. Exp. Med. May 1, 1956;103(5):577-88, see p. 577, second paragraph.*
Ajello et al (Journal of Clinical Microbiology, Jul. 1984, p. 55-58.*
Jennings 1990. Microbial. Immunol. 150, 97-127.
Artenstein, M. S., et al., (1970) New Engl. J. Med. 282, pp. 417-420.
Peltola, H., et al., (1997) New Engl. J. Med 297, pp. 686-691.
Reingold, A. L., et al., (1985) Lancet 2, pp. 114-118.
Brandt, B. L. and Artenstein, M. S. (1975) J. Infect. Diseases. 131, pp. S69-S72.
Kyhty, H., et al., (1980) J. Infect. Diseases. 142, pp. 861-868.
Cessey, S. J., et al., (1993) J. Infect. Diseases. 167, pp. 1212-1216.
Nahm, M. H., M. A. Apicella, and D. E. Briles. 1999. Immunity to extracellular bacteria, p. 1373-1386. In W. E. Paul (ed.), Fundamental immunology, 4th ed. Lippincott-Raven Publishers, Philadelphia, PA.
Mond, J. J., A. Lees, and C. M. Snapper. 1995. T cell-independent antigens type 2. Annu. Rev. Immunol. 13:655-692.
Dick, W. E., Jr., and M. Beurret. 1989. Glycoconjugates of bacterial carbohydrate antigens. A survey and consideration of design and preparation factors. Contrib. Microbiol. Immunol. 10:48-114.
Robbins, J. B., R. Schneerson, P. Anderson, and D. H. Smith. 1996. The 1996 Albert Lasker Medical Research Awards. Prevention of systemic infections, especially meningitis, caused by *Haemophilus influenzae* type b. Impact on public health and implications for other polysaccharide-based vaccines. JAMA 276:1181-1185.
Fu et al., 1995 Biotechnology., vol. 13, pp. 170-174.
Romero, D and Outschoorn I.M. (1994) Clin. Microb. Rev. 7: 559-575.
Frantz, I.D. Jr. Growth Requirements of the Meningococcus. J. Bact., 43: 757-761, 1942.
Catlin, B.W. Nutritional profiles of *Neisseria lactamica, gonorrhoeae* and *meningitidis*, in chemically defined media. J. Inf. Dis., 128(2): 178-194, 1973.
Watson RG, et al. The specific hapten of group C (group IIa) meningococcus, II. Chemical nature. J Immunol 1958; 81:337-44.
Marcelo Fossa Da Paz; Julia Baruque-Ramos; Harolda Hiss; Marcio Alberto Vicentin; Maria Betania Batista Leal; Isaias Raw. Polysaccharide production in batch process of *Neisseria meningitidis* serogroup C comparing Frantz, modified Frantz and Catlin 6 cultivation media, Braz. J. Microbiol. vol. 34., No. 1. São Paulo Jan./Apr. 2003.

(Continued)

*Primary Examiner*—Robert B Mondesi
*Assistant Examiner*—Oluwatosin Ogunbiyi

(57) ABSTRACT

Methods for producing quadrivalent meningococcal meningitis polysaccharide and conjugate vaccines for serotypes A, C, Y and W-135 disclosed. *Neisseria meningitidis* fastidious medium was designed to maximize the yield of capsular polysaccharides and generate minimal cellular biomass and endotoxin in a short duration of fermentation. The crude polysaccharides are isolated, purified, and mechanically depolymerized by sonication. These purified polysaccharides were found in human clinical trials to be safe and immunogenic against meningococcal disease caused by *N. meningitidis* A, C, Y and W-135 serogroups in sub-Saharan Africa. In the preferred embodiment, the polysaccharides are conjugated to carrier proteins of diphtheria or tetanus toxoid to an average molecular size of 5100 to 9900 Daltons and provide broad spectrum protection to humans of all ages. Accelerated polysaccharide production and the efficacy of the resulting vaccine are demonstrated.

18 Claims, 17 Drawing Sheets

OTHER PUBLICATIONS

Cox et.al., (Andrew D Cox, J Claire Wright, Jianjun Li, Derek W Hood, E Richard Moxon, James C Richardes 2003. Phosphorylation of the lipid A region of meningococcal lipopolysaccharide: identification of a family of transferases that add phosphoethanolamine to lipopolysaccharide J Bacteriol. Jun. 2003 ;185 (11):3270-7 12754224.

Gotschlich E.C.; Liu, T.Y.; Artenstein, M.D. Human immunity to the meningococcal—III. preparation and immunochemical properties of the group A, group B, and group C meningococcal polysaccharides. J. Exp. Med., 129 (2): 1349-1365, 1969.

Carty, C.E. et al. Cultivation studies of *Neisseria meningitidis* serogroups A, C, W-135 and Y. Developments in Industrial Microbiology (edited by Merck Laboratories), 25:695-700, 1984.

P Van Der Ley, J E Heckels, M Virji, P Hoogerhout, and J T Poolman Infect Immun. Sep. 1991; 59 (9): 2963-2971.

Aldert Bart et. al., Infection and Immunity, 1999, vol. 67 (8) p. 3842-3846.

Costantino, P., F. Norelli, A. Giannozzi, S. D'Ascenzi, A. Bartoloni, S. Kaur, D. Tang, R. Seid, S. Viti, R. Paffetti, M. Bigio, C. Pennatini, G. Averani, V. Guarnieri, E. Gallo, N. Ravenscroft, C. Lazzeroni, R. Rappuoli, and C. Ceccarini. 1999. Size fractionation of bacterial capsular polysaccharides for their use in conjugate vaccines. Vaccine 17:1251-1263.

Costantino, P., S. Viti, A. Podda, M. A. Velmonte, L. Nencioni, and R. Rappuoli, 1992. Development and phase 1 clinical testing of a conjugate vaccine against meningococcus A and C. Vaccine 10:691-698.

Ravenscroft, N., G. Averani, A. Bartoloni, S. Berti, M. Bigio, V. Carinci, P. Costantino, S. D'Ascenzi, A. Giannozzi, F. Norelli, C. Pennatini, D. Proietti, C. Ceccarini, and P. Cescutti. 1999. Size determination of bacterial capsular oligosaccharides used to prepare conjugate vaccines. Vaccine 17:2802-2816.

Jennings, H.J., and Lugowski, C. 1981. Immunochemistry of group A,B, and C meningococcal polysaccharide-tetanus toxoid conjugates. J. Immunol. 127, 1011-1018.

Svennerholm, L. 1957. Quantitative estimation of sialic acids. II. A colorimetric resorcinol-hydrochloric acid method. Biochim. Biophys. Acta 24:604-611.

Ricci, S., A. Bardotti, S. D'Ascenzi, and N. Ravenscroft. 2001. Development of a new method for the quantitative analysis of the extracellular polysaccharide of *Neisseria meningitidis* serogroup A by use of high-performance anion-exchange chromatography with pulsed-amperometric detection. Vaccine 19:1989-1997.

Giannini, G., R. Rappuoli, and G. Ratti. 1984. The amino-acid sequence of two non-toxic mutants of diphtheria toxin: CRM45 and CRM197. Nucleic Acids Res. 12:4063-4069.

Reddy Jr, Kwang J, Varthakavi V,Lechtenberg KF, Minocha HC. Semiliki forest virus vector carrying the bovine viral diarrhea virus NS3 (p80) cDNA induced immune responses in mice and expressed BVDV protein in mammalian cells. Comp. Immunol. Microbiol. Infect. Dis. Oct. 1999; 22(4):231-46.

Granoff, D. M., and S. L. Harris. 2004. Protective activity of group C anticapsular antibodies elicited in two-year-olds by an investigational quadrivalent *Neisseria meningitidis*-diphtheria toxoid conjugate vaccine. Pediatr. Infect. Dis. J. 23:490-497.

* cited by examiner

FIG. 1: Dry Biomass Production in 100 Liter Bioreactor Average of Neisseria meningitidis serotypes A,C,Y,W-135.

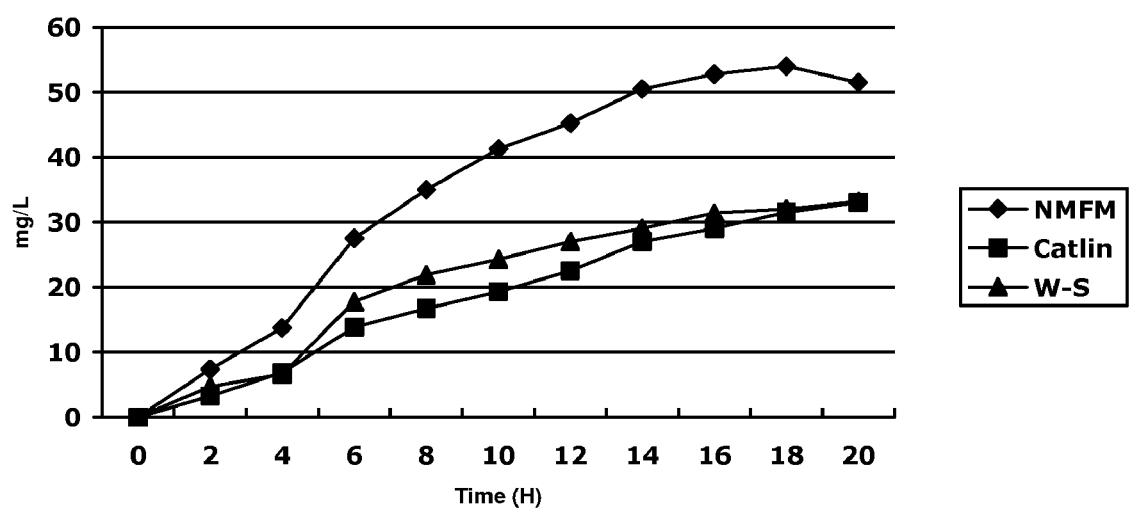
FIG. 2: Comparison of polysaccharide production (mg/L) in 100 L Bioreactor average of Neisseria meningitidis serotypes A, C, FIG. 3: Carbon source concentration (g/L) in 100 L Bioreactor average of Neisseria meningitidis serotypes A, C, Y, and W-135

FIG. 4: pH Shift during fermentation in 100 L bioreactor average of Neisseria meningitidis serotypes A, C, Y, and W-135.

FIG. 5: Neisseria meningitidis serogroup A production in NMFM Media: Polysaccharides (PS) and Toxins (milligrams/liter) in 100 liter Fermentor with 80-liters working volume FIG. 6: Neisseria meningitidis serogroup A production in NMFM Media: X = Bacteria cell concentration (g/L), S = glucose concentration (g/L)

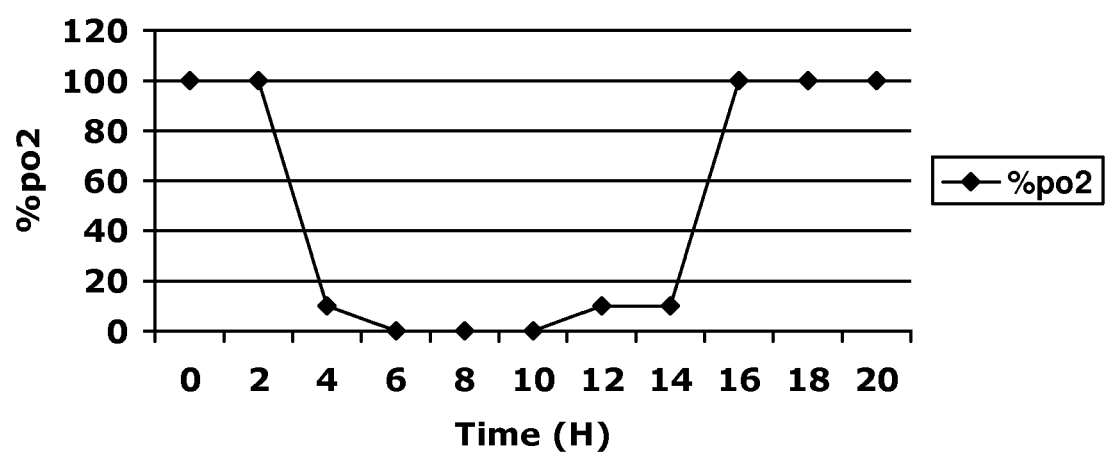
FIG. 7: Neisseria meningitidis Serogroup A production in NMFM medium Oxygen Saturation (%po2)

Fig. 8: Neisseria meningitidis serogroup C production in NMFM Media: Polysaccharides (PS) and Toxins (milligrams / liter) in 100 liter Fermentor with 80-liters working volume.

Fig. 9: Neisseria meningitidis serogroup C production in NMFM Media: X = Cell concentration (g/L), S = glucose concentration (g/L).

FIG. 10: Neisseria meningitidis Serogroup C production in NMFM medium Oxygen Saturation (%po2)

FIG. 11: Neisseria meningitidis serogroup Y production in NMFM Media: Polysaccharides (PS) and Toxins (milligrams / liter) in 100 liter Fermentor with 80-liters working volume.

FIG. 12: Neisseria meningitidis serogroup Y production in NMFM Media: X = Cell concentration (g/L), S = glucose concentration (g/L)

Fig. 13: Neisseria meningitidis serogroup Y production in NMFM medium Oxygen Saturation (%PO2)

FIG. 14: Neisseria meningitidis serogroup W-135 production in NMFM Media: Polysaccharides (PS) and Toxins (milligrams / liter) in 100 liter Fermentor with 80-liters working volume.

FIG. 15: Neisseria meningitidis serogroup W-135 production in NMFM Media: X = Cell concentration (g/L), S = glucose concentration (g/L)

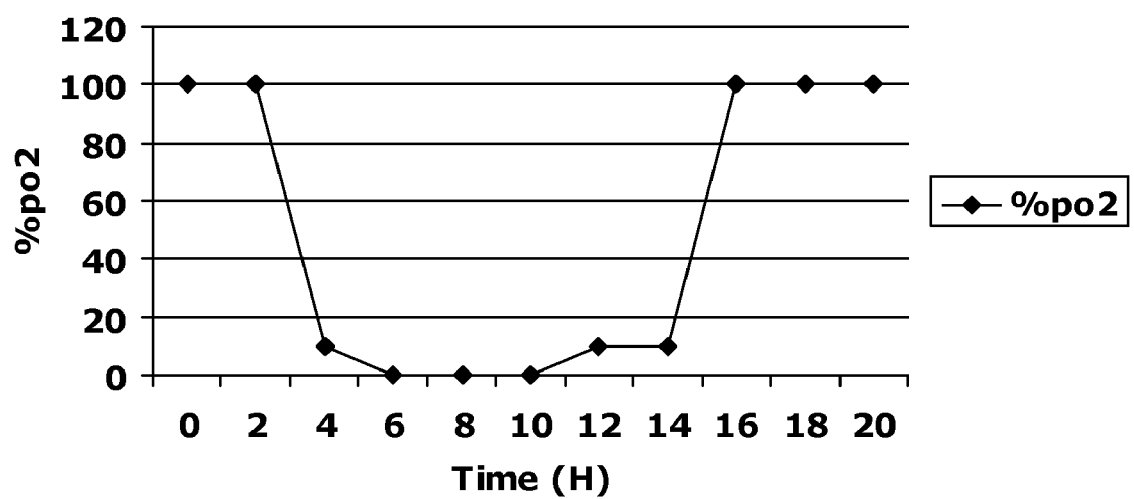
FIG. 16: Neisseria meningitidis Serogroup W-135 production in NMFM medium Oxygen

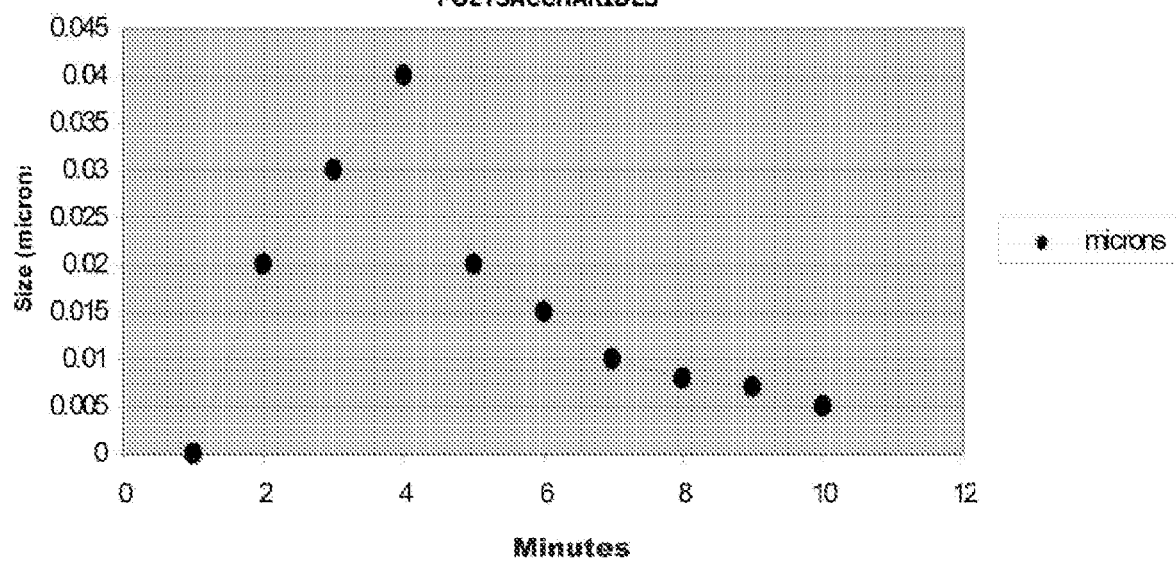
FIG. 17: SONICATION OF POLYSACCHARIDES TO GENERATE MICRO POLYSACCHARIDES

METHOD OF PRODUCING MENINGOCOCCAL MENINGITIS VACCINE FOR *NEISSERIA MENINGITIDIS* SEROTYPES A,C,Y, AND W-135

CROSS-REFERENCE TO RELATED APPLICATIONS

This application is based on provisional application U.S. Ser. No. 60/831,682 filed on Jul. 19, 2006

BACKGROUND OF THE INVENTION

1. Field of the Invention

The present invention relates generally to the field of medical microbiology, immunology, vaccines and the prevention of infection by a bacterial pathogen by immunization.

2. Description of the Related Art

Meningococcal meningitis is an infection of the meninges, the thin lining that surrounds the brain and the spinal cord. The causative agent, *Neisseria meningitidis* (the meningococcus), was identified in 1887. Meningococcal disease was first reported in 1805 when an outbreak swept through Geneva, Switzerland.

Twelve subtypes or serogroups of *N. meningitidis* have been identified and four (*N. meningitidis*. A, B, C and W-135) are known to cause epidemics. The pathogenicity, immunogenicity, and epidemic capabilities differ according to the serogroup. Thus the identification of the serogroup responsible for a sporadic case is crucial for epidemic containment. The most common symptoms are stiff neck, high fever, sensitivity to light, confusion, headaches, and vomiting. Even when the disease is diagnosed early and adequate therapy instituted, 5% to 10% of patients die, typically within 24-48 hours of the onset of symptoms. Bacterial meningitis may result in brain damage, hearing loss, or learning disability in 10 to 20% of survivors. A less common but more severe (often fatal) form of meningococcal disease is meningococcal septicaemia which is characterized by a haemorrhagic rash and rapid circulatory collapse.

Major African epidemics are associated with *N. meningitidis* serogroups A, W-135 and C, and serogroup A is usually the cause of meningococcal disease in Asia. Outside Africa, only Mongolia reported a large epidemic in recent years (1994-95). There is increasing evidence of serogroup W-135 being associated with outbreaks of considerable size. In 2000 and 2001 several hundred pilgrims attending the Hajj in Saudi Arabia were infected with *N. meningitidis* W-135. Then in 2002, W-135 emerged in Burkina Faso, striking 13,000 people and killing 1,500.

The highest burden of meningococcal disease occurs in sub-Saharan Africa, which is known as the "Meningitis Belt", an area that stretches from Senegal in the west to Ethiopia in the east, with an estimated total population of 300 million people. This hyper-endemic area is characterized by particular climate and social habits. During the dry season, between December and June, because of dust winds and upper respiratory tract infections due to cold nights, the local immunity is diminished, increasing the risk of meningitis. At the same time, the transmission of *N. meningitidis* is favored by overcrowded housing at the family level and by large population displacements due to pilgrimages and traditional markets at the regional level. This conjunction of factors explains the large epidemics which occur during this season in the meningitis belt area. Due to herd immunity (whereby transmission is blocked when a critical percentage of the population has been vaccinated, thus extending protection to the unvaccinated), these epidemics occur in a cyclic mode. *N. meningitidis* A, C and W-135 are now the main serogroups involved in the meningococcal meningitis activity in Africa.

In 1996, Africa experienced the largest recorded outbreak of epidemic meningitis in history, with over 250,000 cases and 25,000 deaths registered. Between that crisis and 2002, 223,000 new cases of meningococcal meningitis were reported to the World Health Organization. The countries most affected have been Burkina Faso, Chad, Ethiopia, and Niger. In 2002, the outbreaks occurring in Burkina Faso, Ethiopia, and Niger accounted for about 65% of the total cases reported on the African continent. Furthermore, the meningitis belt appears to be extending further south. In 2002, the Great Lakes region was affected by outbreaks in villages and refugee camps which caused more than 2,200 cases, including 200 deaths.

In 2006 and 2007, outbreaks of the disease occurred in the North of Ivory Coast and the southern region of Burkina Faso, Southern Sudan and UgaNAD (Nicotinamide adenine dinucleotide), killing several children and adults. Meningococcal meningitis is not only important in Africa but also throughout the world. Meningococcal meningitis is considered an important disease not only for sub-Saharan Africa but also for North America, UK, Ireland, Europe, South East Asia, the Middle East, and New Zealand.

The capsular polysaccharides of *Neisseria meningitidis* are attractive vaccine candidates because they constitute the most highly conserved and most exposed bacterial-surface antigens. The use of capsular polysaccharides as immunoprophylactic agents against human disease caused by encapsulated bacteria is now firmly established. The capsular polysaccharides of the meningococcus are negatively charged and are obtained in a high molecular-weight immunogenic form by precipitation. Meningococcal polysaccharide vaccines are efficacious for protection from meningitis disease in adults. The duration of protection elicited by the meningococcal polysaccharide vaccines is not long lasting, and has been estimated to be 18 months in adults and children above four years of age. For children from one to four years old the duration of protection is less than three years.

Polysaccharides themselves are poor at stimulating an effective antibody response in the highest risk age groups (infants). Coupling T-cell independent saccharides to a T-cell dependent protein allows the infant immune system to provide T-cell help to B-cells to produce a boostable IgG antibody of high affinity to the polysaccharide antigen. T-Independent antigens are immunologically important. Molecules such as polysaccharides that have numerous identical evenly spaced epitopes characterize one type of TI antigen. As clusters of B-cell receptors bind the antigen simultaneously, it causes B-cell activation without the help of T-helper cells. These antigens are particularly important in young children who respond poorly to these antigens. Children less than two years of age are more susceptible to diseases caused by microbes that have polysaccharide capsules such as *Neisseria meningitidis*. Discovery of low-cost manufacture of meningitis vaccine is the real objective of this invention to provide affordable vaccine to third world countries to reduce mortality of infants, children, and adults.

Existing State of the Art:

The capsular polysaccharides of *Neisseria meningitidis* are attractive vaccine candidates because they constitute the most highly conserved and most exposed bacterial-surface antigens (Jennings 1990. Microbial. Immunol. 150, 97-127).

The use of capsular polysaccharides as immunoprophylactic agents against human disease caused by encapsulated bacteria is now firmly established. The capsular polysaccharides of the meningococcus are negatively charged and are obtained in a high molecular weight immunogenic form by precipitation. Meningococcal polysaccharide vaccines are efficacious to protect from meningitis disease in adults (Artenstein, M. S., et al., (1970) New Engl. J. Med. 282, pp. 417-420 and Peltola, H., et al., (1997) New Engl. J. Med 297, pp. 686-691), but cannot provide full protection to infants under the age of 5 (Reingold, A. L., et al., (1985) Lancet 2, pp. 114-118).

The duration of protection elicited by the meningococcal polysaccharide vaccines is not long lasting in adults and children above four years of age (Brandt, B. L. and Artenstein, M. S. (1975) J. Infect. Diseases. 131, pp. S69-S72, Kyhty, H., et al., (1980) J. Infect. Diseases. 142, pp. 861-868, and Cessey, S. J., et al., (1993) J. Infect. Diseases. 167, pp 1212-1216).

For children from one to four years old the duration of protection is less than three years (Reingold, A. L., et al., (1985) Lancet 2, pp. 114-118).

Protective immunity to encapsulated bacterial pathogens such as *N. meningitidis* is principally mediated by the reaction between antibody and capsular polysaccharide epitopes. In encapsulated gram-negative bacteria, protection results primarily from a direct complement-mediated bactericidal effect (Nahm, M. H., M. A. Apicella, and D. E. Briles. 1999. Immunity to extracellular bacteria, p. 1373-1386. In W. E. Paul (ed.), FuNAD (Nicotinamide adenine dinucleotide) mental immunology, 4th ed. Lippincott-Raven Publishers, Philadelphia, Pa.).

Vaccines have been prepared from the capsular polysaccharides of *Neisseria meningitidis* (groups A, C, W-135, and Y). These and other polysaccharides have been classified as T cell-independent type 2 (TI-2) antigens based on their inability to stimulate an immune response in animals that carry an X-linked immune B-cell defect (xid) (Mond, J. J., A. Lees, and C. M. Snapper. 1995. T cell-independent antigens type 2. Annu. Rev. Immunol. 13:655-692).

TI-2 antigens tend to be characterized by high molecular weight, multiple repeat epitopes, slow degradation in vivo, and a failure to stimulate major histocompatibility complex (MHC) type II-mediated T-cell help (Mond, J. J., A. Lees, and C. M. Snapper. 1995. T cell-independent antigens type 2. Annu. Rev. Immunol. 13:655-692 and Dick, W. E., Jr., and M. Beurret. 1989. Glycoconjugates of bacterial carbohydrate antigens. A survey and consideration of design and preparation factors. Contrib. Microbiol. Immunol. 10:48-114).

TI-2 antigens generally are incapable of stimulating an immune response in neonatal humans under 18 months of age. This has spurred attempts to modify the capsular polysaccharides such that vaccines protective for all at-risk groups will result. To date, the most successful approach has been to covalently bind carrier proteins to the polysaccharides, thus engendering a vaccine capable of invoking a T-dependent response (Robbins, J. B., R. Schneerson, P. Anderson, and D. H. Smith. 1996. The 1996 Albert Lasker Medical Research Awards. Prevention of systemic infections, especially meningitis, caused by Haemophilus influenzae type b. Impact on public health and implications for other polysaccharide-based vaccines. JAMA 276:1181-11).

Glucose uptake seems to be affected by oxygen concentration and this effect could be related to different levels of carbohydrate metabolism according to higher or lower availability of oxygen (Fu et al., 1995 Biotechnology., vol. 13, pp. 170-174)

Class 4 proteins of *Neisseria meningitidis* are known to be anti-bactericidal. A novel methodology for the purification of polysaccharides to produce toxin-free vaccine, where class 4 were deleted from the vaccine strains, was developed (Romero, D and Outschoorn I. M. (1994) Clin. Microb. Rev. 7: 559-575).

Several synthetic media were discovered for large-scale production of meningococcal polysaccharide (Frantz, I. D. Jr. Growth Requirements of the Meningococcus. J. Bact., 43: 757-761, 1942; Catlin, B. W. Nutritional profiles of Neisseria lactamica, gonorrhoeae and meningitidis, in chemically defined media. J. Inf. Dis., 128(2): 178-194, 1973; Watson-Scherp Medium: Watson R G, et al. The specific hapten of group C (group IIa) meningococcus, II. Chemical nature. J Immunol 1958; 81:337-44; Marcelo Fossa da Paz; Júulia Baruque-Ramos; Haroldo Hiss; Márcio Alberto Vicentin; Maria Betania Batista Leal; Isaías Raw. Polysaccharide production in batch process of *Neisseria meningitidis* serogroup C comparing Frantz, modified Frantz and Catlin 6 cultivation media, Braz. J. Microbiol. vol. 34., no. 1. São Paulo January/April 2003).

Cox et. al., (Andrew D Cox, J Claire Wright, Jianjun Li, Derek W Hood, E Richard Moxon, James C Richards 2003. Phosphorylation of the lipid A region of meningococcal lipopolysaccharide: identification of a family of transferases that add phosphoethanolamine to lipopolysaccharide J Bacteriol. 2003 June; 185 (11):3270-7 12754224.) reported that the NMB1638 gene of *Neisseria meningitidis* was responsible for a lipopolysaccharide (LPS) containing lipid A that was characteristically phosphorylated with multiple phosphate and phosphoethanolamine residues.

Gotschlich E. C.; Liu, T. Y.; Artenstein, M. D. Human immunity to the meningococcal—III. preparation and immunochemical properties of the group A, group B, and group C meningococcal polysaccharides. *J. Exp. Med.*, 129(2): 1349-1365, 1969 reported effective method for purification of meningococcal polysaccharides from liquid cultures.

Cationic reagent Cetavlon™ (hexadecyltrimethyl ammonium bromide) was used to precipitate anionic polysaccharides in this study as per Aymé, G.; Donikian, R.; Mynard, M. C.; Lagrandeur, G. Production and Controls of Serogroup A *Neisseria meningitidis*Polysaccharide Vaccine. *In: Table Ronde Sur L'Immunoprophilaxie de la Meningite Cerebro-Spinale.* Edition Fondation Mérieux, Lyon (France), 1973); Carty, C. E. et al. Cultivation studies of *Neisseria meningitidis* serogroups A, C, W-135 and Y. Developments in Industrial Microbiology (edited by Merck Laboratories), 25:695-700, 1984.

We have chosen ELISA bioassays for the trials because transportation problems of live bacteria from the United States to Africa for performing SBA bioassays.

Meningococcal serogroup A, C, W-135, and Y polysaccharides and DT or CRM197-based conjugates were prepared as already described (Costantino, P., F. Norelli, A. Giannozzi, S. D'Ascenzi, A. Bartoloni, S. Kaur, D. Tang, R. Seid, S. Viti, R. Paffetti, M. Bigio, C. Pennatini, G. Averani, V. Guarnieri, E. Gallo, N. Ravenscroft, C. Lazzeroni, R. Rappuoli, and C. Ceccarini. 1999. Size fractionation of bacterial capsular polysaccharides for their use in conjugate vaccines. Vaccine 17:1251-1263.; Costantino, P., S. Viti, A. Podda, M. A. Velmonte, L. Nencioni, and R. Rappuoli. 1992. Development and phase 1 clinical testing of a conjugate vaccine against meningococcus A and C. Vaccine 10:691-698.; Ravenscroft, N., G. Averani, A. Bartoloni, S. Berti, M. Bigio, V. Carinci, P. Costantino, S. D'Ascenzi, A. Giannozzi, F. Norelli, C. Pennatini, D. Proietti, C. Ceccarini, and P. Cescutti. 1999. Size determination of bacterial capsular oligosaccharides used to prepare conjugate vaccines. Vaccine 17:2802-2816.).

The same conjugation chemistry was used for the preparation of Y constructs (Jennings, H. J., and Lugowski, C. 1981. Immunochemistry of group A, B, and C meningococcal polysaccharide-tetanus toxoid conjugates. J. Immunol. 127, 1011-1018). The polysaccharide content of serogroups C, W-135, and Y conjugates was quantified by sialic acid determination (Svennerholm, L. 1957. Quantitative estimation of sialic acids. II. A colorimetric resorcinol-hydrochloric acid method. Biochim. Biophys. Acta 24:604-611.).

Serogroup A conjugate was quantified by mannosamine-1-phosphate chromatographic determination (Ricci, S., A. Bardotti, S. D'Ascenzi, and N. Ravenscroft. 2001. Development of a new method for the quantitative analysis of the extracellular polysaccharide of Neisseria meningitidis serogroup A by use of high-performance anion-exchange chromatography with pulsed-amperometric detection. Vaccine 19:1989-1997.).

The protein content was measured by a micro-bicinchoninic acid assay of Lowry et al. (1951). The polysaccharide-to-protein ratio of conjugates ranged between 0.3 and 1.5, similar to that of cross-reacting material DT and CRM-based conjugates (Giannini, G., R. Rappuoli, and G. Ratti. 1984. The amino-acid sequence of two non-toxic mutants of diphtheria toxin: CRM45 and CRM197. Nucleic Acids Res. 12:4063-4069).

A lymphocyte proliferation assay was performed according to the method described by us in our journal article (Reddy J R, Kwang J, Varthakavi V, Lechtenberg K F, Minocha H C. Semiliki forest virus vector carrying the bovine viral diarrhea virus NS3 (p80) cDNA induced immune responses in mice and expressed BVDV protein in mammalian cells. Comp. Immunol. Microbiol. Infect. Dis. 1999 October; 22(4):231-46).

In addition, antigenic variation (Antigenic Variation of the Class-1 Outer Membrane Protein in Hyperendemic *Neisseria meningitidis* trains in The Netherlands Aldert Bart et. al., Infection and Immunity, 1999, Vol 67 (8) p.3842-3846) and human complement sensitivity of *Neisseria meningitidis* is a barrier to rely on SBA bioassays.

Conjugation of bacterial polysaccharides to immunogenic carrier proteins generally results in conjugates that induce strong anti-polysaccharide T-helper-cell dependent immune responses in young infants (Granoff, D. M., and S. L. Harris. 2004. Protective activity of group C anticapsular antibodies elicited in two-year-olds by an investigational quadrivalent *Neisseria meningitidis*-diphtheria toxoid conjugate vaccine. Pediatr. Infect. Dis. J. 23:490-497).

The existing state of the art described in the U.S. Pat. No. 4,123,520 for precipitating polysaccharides by a phenol extraction method is found to require more steps for removing the phenol contaminants from the pure polysaccharide mixture. The problem with the invention disclosed in this patent is that the phenol contaminants may interfere with the pure polysaccharide production process.

The existing state of the art described in the U.S. Pat. No. 4,182,751 for precipitating polysaccharides by a phenol extraction for removing the lipopolysaccharide endotoxin from the pure polysaccharide mixture. The problem with the invention disclosed in this patent is that the phenol contaminants may interfere with the pure polysaccharide production process.

The existing state of art described in patent no. WO03007985 for precipitating the polysaccharide with cetalvon and depolymerized chemical hydrolysis. The problem with that invention is the chemical process for depolymerization may interfere with the purity in polysaccharide vaccines production.

U.S. Pat. No. 5,494,808 reports a large-scale, high cell density (5 g/L dry cell weight, and an optical density of between about 10-13 at 600 nm) fermentation process for the cultivation of *N. meningitidis*. The problem with the invention art is that large scale biomass production reduces the production of capsular polysaccharides.

Existing art reported in the U.S. patent publication No. 20060088554 about the depolymerization of polysaccharides and conjugation of polysaccharides with carrier proteins which are activated by chemical means. The problem with this invention is that the chemical residues tend to induce adverse side effects during routine immunization.

U.S. patent publication No: 20050002957 reports depolymerization of polysaccharides by chemical means, which results in producing chemical residues and conjugation of polysaccharides with carrier proteins which are activated chemically, requiring more purification steps. The average size of purified capsular polysaccharides is about 8,000 to 35,000 Daltons, which may not provide efficient immune response in humans.

The existing state of the art described in the patent No WO2005004909 reports, including adjuvant for enhancing immunogenicity against *Neisseria meningitidis* serogroups A, C, W-135, and Y, which may have adverse side effects during routine immunization.

U.S. Pat. No. 6,933,137 claims the development of 'animal free meningococcal polysaccharide fermentation medium', containing soy peptone as a nitrogen source. The problem with this medium is that it requires pH adjustment during the fermentation process. Glucose utilization is higher in this medium, resulting in excessive cellular biomass.

U.S. Pat. No. 6,642,017 relates to methods of modulating capsular polysaccharide production in pneumococci such as Streptococcus pneumoniae. This invention of modulating capsular polysaccharide production is not related to *N. meningitidis.*

Therefore there is a need for an invention to eliminate the short-comings identified in the above prior art and to invent a method of producing a meningococcal meningitis vaccine without any chemical impurities or residues to eliminate the disadvantage of the present state of the art for depolymerization and conjugation by chemical means and capsular polysaccharide size. Also, there is a need for a medium that ensures a higher yield of polysaccharides and lower yield of cellular biomass to facilitate the production and purification processes for vaccine production.

Therefore it is an object of the present invention to invent a method of producing meningococcal meningitis vaccine comprising *N. meningitidis* serotypes A, C, Y and W-135 that have long lasting effect and provide broad spectrum immunity to humans of all age groups.

It is yet another object of the present invention to develop a method wherein trace chemical impurities currently present in the available meningococcal meningitis vaccine are eliminated by a mechanical method, preferably sonication.

Another object of the present invention is to invent a composition of a medium that yields a higher percentage of polysaccharides in comparison to known media employed for producing meningococcal meningitis vaccine.

It is yet another object of the present invention to invent a composition of a medium that yields a lower percentage of cellular biomass in comparison with known media employed for producing meningococcal meningitis vaccine.

It is yet another object of the invention to identify an optimum molecular size of *N. meningitidis* polysaccharides of serogroups A, C, Y and W-135 that confers broad spectrum immunogenic protection against meningitis.

BRIEF SUMMARY OF THE INVENTION

Methods for producing quadrivalent meningococcal meningitis polysaccharide vaccine for serotypes A, C, Y and W-135 by mechanical means: The methods employ *Neisseria meningitidis* fastidious medium specially designed to maximize the yield of capsular polysaccharides and minimize yield of the cellular biomass and endotoxins. The crude polysaccharides are isolated and purified by ultra-filtration and gently treated with a polycationic compound that precipitates the polyanionic capsular polysaccharides and to maximize the yield of precipitated polysaccharides from liquid cultures. The polysaccharides are then mechanically depolymerized, preferably by sonication. The pure polysaccharides were found in human clinical trials to be highly effective against meningitis caused by *N. meningitidis* A, C, Y and W-135 serogroups. In the most preferred embodiment the pure polysaccharides are conjugated to carrier proteins of diphtheria or tetanus toxoid to provide broad spectrum protection to humans of all age groups.

The present invention is directed to a method of producing meningococcal meningitis vaccine in the *Neisseria meningitidis* fastidious medium with composition of medium comprising DI water, NaCl, K2SO4, KCl, Trisodium citrate.2H2O, MgSO4.7H2O, MnSO4.H2O, MnCl2.6H2O, Vitamin B12 (source: *Saccharomyces cerevisiae*), NAD (Nicotinamide adenine dinucleotide), Thiamine HCL, Soy peptone, D-Glucose, L-Glutamic acid, L-Arginine, L-Serine, L-Cysteine, Glycine, Morpholinepropanesulphonic acid [MOPS], CaCO3 with the PH maintained at 6.5 to 7.0 (Fe2 (SO4)3 for seogroup A and NH4Cl for serogroup W-135). The specific formulation used in the experiments conducted is given below.

*Neisseria Meningitidis* Fastidious Medium (NMFM) for serogroups A, C, Y and W-135: (grams per Liter)

| Components: with the PH maintained at 6.5 to 7.0 | Quantity (g/L) | Concentration (mM) |
|---|---|---|
| DI water | 900 mL | |
| NaCl | 0.35 g | |
| K2SO4 | 0.20 g | |
| KCl | 0.20 g | |
| Trisodium citrate•2H2O | 0.70 g | |
| MgSO4•7H2O | 0.60 g | |
| MnSO4•H2O | 1.00 mg | |
| MnCl2•6H2O | 40 mg | |
| Vitamin B12 (source: *Saccharomyces cerevisiae*) | 10.0 g | |
| NAD (Nicotinamide adenine dinucleotide) | 0.25 g | |
| Thiamine HCL | | |
| Soy peptone | 15 g | |
| D-Glucose | 10 g | |
| L-Glutamic acid | | 5.10 |
| L-Arginine | | 0.237 |
| L-Serine | | 0.476 |
| L-Cysteine | | 0.254 |
| Glycine | | 1.998 |
| Morpholinepropanesulphonic acid [MOPS] | | 10 |
| CaCO3 | | 0.25 |

* $Fe_2(SO_4)_3$ = 0.5 g/L for serogroup A
* NH4Cl = 1.25 g/L for serogroup W-135

Filter sterilized glucose and amino acids were added to the autoclaved cool medium, which improved production of polysaccharides by 25%. This type of process allowed non-degradation of heat sensitive sugars and amino acids and eliminated batch feeding during the fermentation process for polysaccharide production. The above medium is specially designed to increase the production of capsular polysaccharide and decrease the production of cellular biomass. One more special feature of the medium is that the pH is maintained from about 6.5 to about 7.0 during the fermentation process without using buffers and pH probes. Here in this invention the phenol extraction step is replaced by activated carbon filtration to avoid any phenol interaction in purification processes. The isolated polyanionic polysaccharides are then precipitated with a polycationic compound. The precipitated polysaccharides are then subjected to ultra-filtration for the isolation of pure polysaccharides. The isolated pure polysaccharides are depolymerized by sonication. These low molecular weight polysaccharides proved very effective when compared with other inventions. The human trials for pure polysaccharides of serotypes A, C, Y and W-135 in this invention indicated very mild adverse side effects, none of which were severe, and also proved to be very effective for humans above the age of 13 years and may provide effective protection against meningococcal meningitis for humans above the age of 5 years.

In another preferred embodiment the pure low molecular weight polysaccharides were conjugated to carrier proteins of diphtheria or tetanus toxoids to produce quadrivalent meningococcal meningitis conjugated vaccine for the serotypes A, C, Y and W-135. This conjugated vaccine proved effective for all ages. The vaccine proved to be non-toxic and immunogenic in animal trials using neonatal mice and mice of 7-8 weeks, when compared with the known state of the art. The use of mice models in animal trials may show that the conjugated quadrivalent polysaccharide vaccine A, C, Y and W-135 may also be effective for at risk age groups of the children below 2 years and can immunize effectively humans of all ages.

BRIEF DESCRIPTION OF THE SEVERAL VIEWS OF THE DRAWINGS

FIG. 1 is a chart showing a comparison of dry biomass production resulting from the culture of *N. meningitidis* in *Neisseria meningitidis* fastidious medium, Watson-Scherp medium and Catlin medium according to the method of preparation of meningococcal vaccine in the present invention.

FIG. 2 is a chart comparing polysaccharide production for the culture media of FIG. 1

FIG. 3 is a chart comparing carbon source concentration for the culture media of FIG. 1

FIG. 4 is a chart showing the pH shift during fermentation for the culture media of FIG. 1

FIG. 5 is a chart showing *Neisseria meningitidis* serogroup A production in NMFM media for Polysaccharides (PS) and toxins (mg/l) in 100L fermentor with 80L working volume according to the present invention.

FIG. 6 is a chart showing *Neisseria meningitidis* serogroup A production in NMFM media for X=bacterial cell concentration (g/L), S=glucose concentration (g/L) according to the present invention.

FIG. 7 is a chart showing *Neisseria meningitidis* serogroup A production in NMFM media for percentage of oxygen saturation according to the present invention.

FIG. 8 is a chart showing *Neisseria meningitidis* serogroup C production in NMFM media for Polysaccharides (PS) and toxin (mg/L) in 100L fermentor with 80 L working volume according to the present invention.

FIG. 9 is a chart showing *Neisseria meningitidis* serogroup C production in NMFM media for X=cell concentration (g/L), S=glucose concentration (g/L) according to the present invention.

FIG. 10 is a chart showing *Neisseria meningitidis* serogroup Y production in NMFM media for percentage of oxygen saturation according to the present invention.

FIG. 11 is a chart showing the *Neisseria meningitidis* serogroup Y production in NMFM media for Polysaccharides (PS) and toxins (mg/L) in 100L fermentor with 80L working volume according to the present invention.

FIG. 12 is a chart showing *Neisseria meningitidis* serogroup Y production in NMFM media for X=cell concentration (g/L), S=glucose concentration according to the present invention.

FIG. 13 is a chart showing *Neisseria meningitidis* serogroup Y production in NMFM media for percentage of oxygen saturation) according to the present invention.

FIG. 14 is a chart showing *Neisseria meningitidis* serogroup W-135 production in NMFM media for Polysaccharides (PS) and toxins (mg/L) in 100L fermentor with 80L working volume according to the present invention.

FIG. 15 is a chart showing *Neisseria meningitidis* serogroup W-135 production in NMFM media for X=cell concentration (g/L), S=glucose concentration according to the present invention.

FIG. 16 is a chart showing *Neisseria meningitidis* serogroup Y production in NMFM media for percentage of oxygen saturation) according to the present invention.

FIG. 17 is a chart showing Sonication of polysaccharides to generate micro polysaccharides according to the present invention.

Similar reference characters denote corresponding features consistently throughout the attached drawings

DEFINITION

NMFM or NM Fastidious Medium indicates *Neisseria meningitidis* Fastidious Medium.

DETAILED DESCRIPTION OF THE INVENTION

*N. meningitidis* serogroup A, C, Y and W-135 Polysaccharides comprise the vaccine against meningitis. The goal of this experiment was to compare our invented medium with two commonly used cultivation media for production of polysaccharides. Our NM Fastidious Medium (NMFM) was compared with Watson-Scherp and Catlin Media, The comparative criteria were based on the final polysaccharide concentrations and the yield coefficient cell/polysaccharide ($Y_{P/X}$). The kinetic parameters: pH, substrate consumption and cell growth. Cultivation of meningococcal serotypes was carried out in a 100 L New Brunswick® bioreactor, under the following conditions: 80 L of culture medium, temperature 35° C., 6% $CO_2$, air flow 5 L/min, agitation frequency 120 rpm and vessel pressure 6 psi, without dissolved oxygen or pH controls. The cultivation runs were divided in three groups, with 3 repetitions each. The cultivations using NM Fastidious Medium (NMFM) presented the best results: average of four serotypes final polysaccharide concentration at 12 hours in 80 Liters=45.25 mg/L and $Y_{P/X}$=0.13, followed by Watson-Scherp medium with results of 27.00 mg/L and $Y_{P/X}$=0.07 and Catlin medium results of 22.5 mg/L and $Y_{P/X}$=0.05 a respectively. The principal advantage we claim here is in the use of the NMFM for better vaccine production or polysaccharide yield than Watson-Scherp and Catlin media.

DETAILED DESCRIPTION OF THE PREFERRED EMBODIMENT I

Several synthetic media were discovered for large-scale production of meningococcal polysaccharide. Polysaccharide production in batch process of *Neisseria meningitidis* serogroup C comparing Frantz, modified Frantz and Catlin 6 cultivation media. None of these media eliminated the problems associated with longer duration of fermentation process and limitations on endotoxin production. Greatest emphasis was placed on the cost of media components, not on the time associated with the fermentation process or endotoxin removal expenses and time associated with the production of meningococcal polysaccharide vaccine. Though NMFM medium is more expensive to make than other synthetic media, large-scale production of meningococcal polysaccharide using NMFM medium eliminates the longer fermentation process. A major advantage of NMFM medium is the elimination of endotoxin in the polysaccharide purification process for a given time.

The aim of the study was to describe the dynamic behavior of the bioprocess system of *Neisseria meningitidis* that can be used in future control and optimization of the industrial process of capsular polysaccharide production. Inoculation procedure and cultivation conditions were as described later in the document. Samples of the cultivation medium were collected at pre-established time intervals and analytical assays were conducted to obtain microbial growth, glucose uptake, and polysaccharide time profiles. An analysis of the kinetics of capsular polysaccharide production by *Neisseria meningitidis* serogroups was conducted. Based on microorganism behavior and transient characteristics common to processes operated in batch operation mode, such as variations in glucose concentration, accumulation of metabolic products, and availability of dissolved oxygen, a standard set of bioprocess conditions was developed.

Microbial growth: It was observed that the growth rate was greatly dependent on oxygen concentration in the cultivation medium. The specific microbial growth rate was directly proportional to the concentration of dissolved oxygen in the cultivation medium. Microbial growth was limited by concentration of glucose and no growth substrate inhibition effects were observed at the glucose concentration studied in this work. Glucose consumption also seems to be affected by the availability of dissolved oxygen. At the logarithmic phase, the bacterial growth in the medium showed high oxygen concentration and lower glucose uptake that was much lower than the highest specific microbial growth rates. Glucose uptake increased when an oxygen concentration of zero was achieved. Glucose metabolism by *Neisseria meningitidis* was determined by the availability of oxygen. A buildup of capsular polysaccharide formation occurred because the limited availability of oxygen favored the specific polysaccharide production of serotypes A, C, Y, and W-135. The existence of a maximum quantity of surface polysaccharide for each serotype was observed under the conditions described above.

The process of capsular polysaccharide production by *Neisseria meningitis* serogroups was performed in a 100 Liter bioreactor. Experimental results showed that the availability of dissolved oxygen in the cultivation medium determined kinetics of the *N. meningitidis* bacterium. Conditions of higher concentration of oxygen favored microbial growth and decreased the specific capsular polysaccharide production. This could be related to the use of a common lipid intermediate, either in the construction of cell walls, an essential structure for bacterial survival, or in the biosynthesis of capsular polysaccharide. The more rapid accumulation of capsules under conditions of low concentration of dissolved oxygen could also be associated with the need to produce this cell protection structure in situations of stress, such as limited availability of oxygen. Glucose uptake also seems to be affected by oxygen concentration, and this effect could be related to different rates of carbohydrate metabolism according to higher or lower availability of oxygen.

The presence of Class 4 proteins of Neisseria meningitidis is known to be anti-bactericidal. Therefore we used Neisseria meningitidis serogroups A, C, Y and W-135 vaccine strains, which were deleted for Class 4 proteins, in vaccine production by the purification of polysaccharides using novel methodology to produce toxin-free vaccine.

Immunogenicity, pyrogenicity, and toxicity of purified polysaccharides were determined in animals and humans. Immunogenicity of vaccine candidates tested by ELISA and Serum Bactericidal Assays (SBA) using animal and human sera showed high serum titers in SBA and high reactivity titers in ELISA in vitro experiments.

Invention of Low Molecular Weight Polysaccharides for Meningococcal Meningitis Vaccine—Preparation and Formulation.

Natural meningococcal polysaccharide is about 500,000 to 1,500,000 daltons. A novel extracellular low-molecular-weight polysaccharide was detected within extracellular class 4 deleted mutants of *Neisseria meningitis* serotype cultures.

The present invention is directed towards a non-chemical method (sonication) to make low molecular weight polysaccharides and to produce conjugated meningococcal polysaccharides with minimum range of 5100 to 9900 Daltons size.

Compositional analysis, methylation analysis, and nuclear magnetic resonance analysis revealed that this low-molecular-weight polysaccharide was composed of the same polysaccharide repeating unit previously described for the high-molecular-weight form of the polysaccharides synthesized from *Neisseria meningitis* serotypes.

The purified polysaccharides contain high molecular and low molecular weight form of Extracellular polysaccharides (EPS). Magnetic sonication was done at 4° C. for 2 hours to obtain soluble low molecular weight EPS. The soluble EPS was collected and analyzed by Mass spectrometry analysis which indicated that the size of this low-molecular-weight form of EPS was consistent with a dimeric form of the polysaccharide repeating unit. High-molecular-weight EPS was then removed from concentrated supernatants by centrifugation (12,000×g for 10 min). Low-molecular-weight, ethanol-soluble polysaccharides were then purified from concentrated supernatants using gel permeation chromatography.

EXAMPLE 1

Fermentation Procedure:

The working Seed Bank stocks of *Neisseria meningitidis* A, C, Y, W-135 were kept frozen in glycerol solution at −80° C. The stock tubes were thawed in running cold water and the outer surface of the tube is disinfected with ethanol, and butterfly streaked with a loop-full of culture of *Neisseria meningitidis* onto two Columbia agar plates. The plates were incubated overnight (18 hours) at 37° C. in an incubator with 6% $CO_2$ atmosphere. The cultures were re-streaked on fresh plates to isolate pure cultures of *Neisseria meningitidis* and incubated at 37° C. in 6% $CO_2$ atmosphere overnight for 12 hours. Bacterial colonies from two plates were collected with a sterile cotton swab and suspended in two 10 ml aliquots of Shedulars broth®(Remel, Inc®) in separate 15 ml centrifuge tubes and re-suspended into 50 ml media contained in a 200 ml flask. The bacteria were allowed to grow at 35° C. under normal atmospheric pressure shaking the flask at 125 rpm for about 3 hours and then transferred from the flask into one 1 Liter flask containing 200 ml pre-warmed medium and the flask was incubated in a shaker at 36° C. at 125 rpm for 12 hours to form a seed culture. An absorbance of 1.5 at 600 nm is considered equivalent to 500 Klett units. The culture was then transferred to a 2 Liter conical flask, containing 500 ml of the same medium, inoculated with 50 ml of the inoculum and incubated under the conditions previously described. The contents of eight of these conical flasks (the ratio of inoculum to the media is 1:10 or 8 L to 80 L) were used as inoculum for the bioreactor (New Brunswick® model MPP 80—total capacity 100 L) with 80 L of medium (Table 1). The cultivation conditions were: temperature 35.0° C.; air flow rate 5 L/min (0.125 vvm, superficial aeration); agitation frequency 120 rpm (with 2 Rushton six blade disc turbines); vessel head space pressure 6 psi; height and diameter of the vessel 72 and 40 cm, respectively; turbine diameter 16.5 cm, one located at 10 cm from the vessel bottom and the other at 35 cm. Four baffles were installed, in order to enhance the mixture efficiency. The oxygen volumetric transfer coefficient ($k_La$) was near 0.07 $min^{-1}$ before the inoculation (t=0 h). The batch cultivation runs, all under the same operational conditions, were divided into three groups, each one with three repetitions: the first one with Watson-Scherp medium, the second employing the Catlin medium; and the third, with NMFM medium.

Analysis:

Cell Concentration was articulated as dry biomass, as determined by centrifugation of a sample at 10,000×g, followed by drying the pellet at 60° C. for 48 hrs. Polysaccharide concentration was assessed after bacterial cell removal and was precipitated by adding Cetavlon™ to the sample. The supernatant was removed after centrifugation and the precipitated biomass re-suspended in a one Molar $CaCl_2.2H_2O$ solution and the supernatant collected for polysaccharide determination using the following method: a sample containing 10-70 g of sialic acid in a 16×150 mm glass tube with the sample volume brought up to 500 g/L. Standard solutions of sialic acid were prepared using 20, 40, 60, 80, and 100 μg, and each was made up to 500 g/L to which was added 50 microliters resorcinol reagent. The tubes were placed in a boiling water bath for 15 min. If the tube shows blue/purple/brown color, it indicates that the sample contains sialic acid. No blue color means that sialic acid is absent. A dark brown color indicates that the sample has either too high a concentration of sialic acid or that it is not pure enough. The tubes were cooled to room temperature (20-25° C.) in a cold water bath and 1 mL (2× sample volume) extraction organic solvent was added into each test tube. The tubes were shaken vigorously and left at room temperature until the organic solvent layer separates completely from the aqueous phase. The top organic phase was transferred to a curvet and the absorbance determined against pure organic solvent in a spectrophotometer at 580 nm. Absorbance was compared with a standard curve for quantification, which detects the polysaccharide monomers (sialic acids) formed after acid hydrolysis. Yield coefficient was calculated by the ratio between polysaccharide production and cell biomass generated ($Y_{P/X}$) at a given cultivation time. FIGS. 1 and 2 show the production associated with polysaccharide in the bacterial population up to the $20^{th}$ hour of incubation.

The graphs, showing the kinetic behavior of each group of experiments (defined in Table 1, 2, and 3) are shown in FIGS. 1, 2, 3 and 4.

The tables given below disclose the compositions of the culture medium therein.

*Neisseria Meningitidis* Fastidious Medium (NMFM) for serogroups C, Y and W-135: (grams per Liter)

| Components: with the PH maintained at 6.5 to 7.0 | Quantity (g/L) | Concentration (mM) |
|---|---|---|
| DI water | 900 mL | |
| NaCl | 0.35 g | |
| K2SO4 | 0.20 g | |
| KCl | 0.20 g | |
| Trisodium citrate•2H2O | 0.70 g | |
| MgSO4•7H2O | 0.60 g | |
| MnSO4•H2O | 1.00 mg | |
| MnCl2•6H2O | 40 mg | |
| Vitamin B12 (source: *Saccharomyces cerevisiae*) | 10.0 g | |
| NAD (Nicotinamide adenine dinucleotide) | 0.25 g | |
| Thiamine HCL | | |
| Soy peptone | 15 g | |
| D-Glucose | 10 g | |
| L-Glutamic acid | | 5.10 |
| L-Arginine | | 0.237 |
| L-Serine | | 0.476 |
| L-Cysteine | | 0.254 |
| Glycine | | 1.998 |
| Morpholinepropanesulphonic acid [MOPS] | | 10 |
| CaCO3 | | 0.25 |

* $Fe_2(SO_4)_3$ = 0.5 g/L for serogroup A
* $NH_4Cl$ = 1.25 g/L for serogroup W-135

Watson-Scherp Medium: grams/Liter: Sodium phosphate, dibasic 2.500; Soy peptone 5-30; Monosodium Glutamate 5.000; Potassium Chloride 0.103; Magnesium sulfate 0.732; L-Cysteine 0.016; Glucose 11.250

Catlin Medium (MCDA) Catlin, (in mM: NaCl, 100; KCl, 2.5; NH.sub.4Cl, 7.5; Na.sub.2HPO.sub.4, 7.5; KH.sub.2PO.sub.4, 1.25; Na3C6.H5.O7.2H20, 2.2; MgSO.sub.4.7H.sub.20, 2.5; MnSO.sub.4.H.sub.20, 0.0075; L-glutamic acid, 8.0; L-arginine.HCl, 0.5; glycine, 2.0; L-serine, 0.2; L-cysteine HCl.H.sub.20, 0.06; sodium lactate, 6.25 mg of 60% syrup/mL of medium; glycerin, 0.5% (v/v); washed purified agar, 1% (wt/vol) CaCl.sub.2.2H.sub.2O, 0.25; Fe.sub.2(SO.sub.4).sub.3, 0.01)

Kinetics:

Kinetics of glucose consumption verses pH was evaluated for the various media. When the Watson-Scherp medium was used (FIG. 2 and FIG. 4), 6 g/L of glucose consumption was observed at the end of the cultivation; with NMFM medium the residual concentration of the substrate was 3 g/L and with Catlin medium glucose consumed was between 5-6 g/L. The consumption of glucose (FIG. 4) during cultivation yielded acid metabolites. These results indicate that the Watson-Scherp medium and Catlin medium require adjustment of pH during the fermentation process. NMFM medium does not require adjustment of the pH throughout cultivation for polysaccharide or vaccine production and provides minimal stress on the bacteria during the fermentation process. This fact indicates that, not only were there no acid metabolites, but also that sequential consumption of amino acids as a source of carbon may have been taken place (FIG. 2).

The association between polysaccharide production and biomass is extremely important in endotoxin-free large-scale production. During cultivation of *N. meningitidis* serogroups A, C, Y, W-135 in a bioreactor and the purification process of the capsular polysaccharide, it is crucial to pay attention to two criteria: attaining the maximum polysaccharide concentration at the end of the cultivation in the bioreactor ($P_f$) and simultaneously attaining the minimum cell debris (biomass) yield factor ($Y_{P/X}$) which is important in the polysaccharide purification process. The rest of the cell debris is nothing but endotoxin contaminant which must be removed in the purification process. FIG. 1 shows average dry biomass concentration from Watson-Scherp, Catlin Medium and NMFM media, where Watson-Scherp produced 0.55 g/L, Catlin 0.45 g/L and NMFM 0.32 g/L at 12 hours.

Statistical Analysis:

Statistical analysis was performed using test "t" at the 5% significance level to compare the data obtained from three media used in this study. Greater final concentrations of polysaccharide (P) and greater cell/polysaccharide yield factors ($Y_{P/X}$) were obtained in the group of experiments 1 to 3 where the NMFM medium was used and resulted in an average of 45.25 mg/L. In addition, statistical tests on the biomass values determined at the end of the cultivations ($X_{max}$) showed that the use of Watson-Scherp medium resulted in production of a large biomass of *N. meningitidis* and did not give the best values for the yield factor ($Y_{P/X}$), compared to experiments carried out using the NMFM medium. This implies that there is a higher concentration of dry cellular biomass production when using Watson-Scherp medium and the lowest was found when using NMFM medium.

The results obtained from the experiments that used the NMFM medium with a glucose concentration of 10.0 g/L, showed that the residual glucose value at the end of the cultivation was lower than that obtained in Watson-Scherp medium and Catlin medium (FIG. 3). Kinetics of nitrogen consumption by *N. meningitidis* during polysaccharide production using the NMFM medium showed that adding the nitrogen source, in the presence of excess glucose, resulted in a greater production of polysaccharides. In 12 hours, the polysaccharide production using NMFM medium showed 45.25 mg/L at neutral pH, minimal dry mass of 0.32 g/L with lower utilization of carbon source compared to Watson-Scherp and Catlin media. The advantages of the NMFM medium are lower costs and easier cultivation and purification stages in the polysaccharide production process.

Procedure for the Production of Capsular Polysaccharide

Capsular polysaccharide production by *Neisseria meningitidis* serogroups A, C, Y, and W-135 was studied in batch experimental runs. The experiments were conducted in a set of 100 L bioreactors with 80% of NMFM cultivation medium. Cultivation temperature and pH were controlled at optimal pre-established values. The dynamic behavior of the bacteria was analyzed based on biomass growth, glucose uptake, polysaccharide production, and dissolved oxygen time profile obtained in a set of experimental runs with initial concentrations of glucose that varied from 5 to 13.5 g/L.

FIGS. 5 to 16 contain the results for runs in 100 L bioreactors with a defined glucose concentration of 10 g/L with working volume of 80 L.

FIGS. 5 to 16 illustrate the polysaccharide production, toxin concentrations, glucose consumption, bacterial cell concentrations, and oxygen saturations for serogroups A, C, Y, and W-135 using NMFM medium. FIGS. 5-16 show a reduced specific rate of microbial growth and endotoxin production following the decrease in availability of dissolved oxygen. These figures also show both the reduced rate of glucose consumption in the region of maximum oxygen concentration and increased consumption under conditions of limited availability of oxygen.

The preset set of controlled conditions for the production of polysaccharides maximized the accumulation of polysaccharides, low biomass, and endotoxin accumulation due to the lack of new bacterial cell formation. Although the glucose was completely consumed, there was no significant difference in the final concentration of polysaccharide between the bioreactor runs using individual serotypes of *N. meningitidis*. Final concentrations of biomass were very similar among all serotypes for all experimental runs. The medium formulation of NMFM has limited phosphate availability, and resulted in lower biomass production, glucose consumption, endotoxin concentration, dissolved oxygen, better pH balance, and greater polysaccharide production for all *Neisseria meningitidis* serotypes. Thus, the designed preset conditions shall be employed for implementation of future optimization of the process for Meningococcal meningitis serotypes A, C, Y, and W-135 polysaccharide vaccine production. The optimized NMFM medium can be employed in implementation of strategies of process control and optimization that aim at maximizing industrial scale Meningococcal meningitis serotypes A, C, Y, and W-135 polysaccharide vaccine production.

Concept for *Neisseria Meningitidis* Medium Invention:

NMFM medium is a highly-enriched bacteriological medium useful for growing fastidious bacteria. The bacterial cell growth in this medium is faster than in other known synthetic and non-synthetic media. NMFM is useful for production of high quantities of toxin-free polysaccharide in a duration of less than or equal to 12 hours. Filter sterilized glucose and amino acids were added to the autoclaved cool medium, which improved production of polysaccharides by 25%. This type of process allowed non-degradation of heat sensitive sugars and amino acids and eliminated batch feeding during the fermentation process for polysaccharide production. Use of NMFM medium for Meningococcal meningitis vaccines saves almost 50% cut-off time in the fermentation process and purification of toxins, and results in clinically-proven safer vaccine production as compared to the use of Watson-Scherp and Catlin media, which require longer periods of fermentation and a more intensive toxin purification process. We used calcium carbonate ($CaCO_3$) to balance the pH of the medium, as opposed to the use of calcium chloride ($CaCl_2$), which can make media more alkaline during fermentation. Ionized calcium is the key buffer that helps to maintain the acid/alkaline balance in NMFM medium. We allowed the mutant strains of *Neisseria meningitidis* serotypes to grow slowly in a short period of incubation to reach lower maximal optical density and to produce more endotoxin-free polysaccharides (PS) than the use of standard media. Cox et. al., reported that the NMB1638 gene of *Neisseria meningitidis* was responsible for a lipopolysaccharide (LPS) containing lipid A that was characteristically phosphorylated with multiple phosphate and phosphoethanolamine residues. Mass spectroscopic analyses of the LPS of *Neisseria meningitidis* strains that had been inactivated by a specific mutation indicated that there were no phosphoethanolamine residues. *Neisseria meningitidis* produces two types of toxins called exotoxins and endotoxins. Exotoxins are released from bacterial cells and may act at tissue sites removed from the site of bacterial growth. Endotoxins are cell-associated substances that are structural components of the cell walls. However, endotoxins are released from growing bacterial cells or from cells which are lysed as a result of effective host defense. Hence, bacterial toxins, both soluble and cell-associated, may be transported by blood and lymph and cause adverse reactions in humans. Lipopolysaccharides are considered the major endotoxin in polysaccharide production. Removal of or minimal supplementation of organic phosphates from liquid cultures is very important in meningococcal polysaccharide production in order to reduce the production of endotoxins.

Gotschlich et. al, first reported effective method for purification of meningococcal polysaccharides from liquid cultures. Cationic reagent Cetavlon™ (hexadecyltrimethyl ammonium bromide) was used to precipitate anionic polysaccharides.

Inorganic phosphates ($P_i$) are required for any bacterium to function as constituents of nucleic acids, nucleotides, phospholipids, lipopolysaccharides (LPS) or toxins, and teichoic acids. In phosphate-deficient NMFM medium, the bacterium utilizes its intracellular phosphate reserve for its cellular function at minimum rates for production and release of undesirable LPS, or toxins, into the medium at minimal level. The NMFM medium does contain minimal inorganic phosphate ($P_i$) salts, but is buffered by 10 mM morpholinepropanesulfonic acid (MOPS; pH 7.0). Due to the stress induced by pH balance combined with ($P_i$) deficiency of the medium, NMFM medium allowed mutant strains of *Neisseria meningitidis* serotypes to grow more slowly, reach lower maximal optical densities, produce less toxins, and produce more polysaccharides (PS) than the standard media. *Neisseria meningitidis* serotypes synthesize capsular polysaccharides that are used as vaccine candidates. These molecules are produced by bacterium as a capsule under strong stressful conditions (both nutritional and physiological stress as stated above) that are tightly associated with the cell assembled as capsular polysaccharides (CPS) which surround the cell surface. When they are liberated into the medium they are called extracellular polysaccharides (EPS).

The capsule expressed by *N. meningitidis* is categorized as a group II capsule based on the similar chemical and physical properties of capsular polymers. Serogroup A is composed of ($\alpha$1→6)-linked N-acetylmannosamine-1-phosphate. The capsules expressed by each of the other major invasive meningococcal serogroups Y and W-135 are composed of alternating units of D-glucose and D-galactose and sialic acid, respectively. The capsular polysaccharides of serogroups C are composed entirely of sialic acid in an ($\alpha$2→8) or an ($\alpha$2→9) linkage.

Phosphatase activity ($P_i$) and pH balance induced increased polysaccharide production by *Neisseria meningitidis* isolates. Data are the average of the means of at least three independent experiments in which each experimental mean was derived from PS extracts of three separate cultures. Cells were incubated 12 h in NMFM with (+) or without (−) phosphorus.

The tables below indicate the phosphatase activity of the respective serogroups shown below. (+) plus phosphates ($+P_i$) in the tables below indicate, Thiamine pyrophosphate 0.10 g; $K_2HPO_4$ 4.00 g, $Na_2HPO_4$ 7.5. (−) minus phosphates ($-P_i$) in the tables below indicate, Morpholinepropanesulfonicacid (MOPS; pH 7.0).

| PHOSPHATASE ACTIVITY | Serogroup A | | | |
|---|---|---|---|---|
| | Culture Phosphate | | Assay pH | |
| mg-polysaccharides | +plus | −minus | 5.0 | 7.0 |
| 0 hours | 0 | 0 | 0 | 0 |
| 3 hours | 8 | 7.2 | 0.92 | 7.2 |
| 8 hours | 17 | 35 | 0.8 | 35 |
| 12 hours | 20 | 43 | 0.4 | 43 |

| PHOSPHATASE ACTIVITY | Serogroup C | | | |
|---|---|---|---|---|
| | Culture Phosphate | | Assay pH | |
| mg-polysaccharides | +plus | −minus | 5.0 | 7.0 |
| 0 hours | 0 | 0 | 0 | 0 |
| 3 hours | 3 | 9 | 0.85 | 9 |
| 8 hours | 15 | 39 | 0.8 | 39 |
| 12 hours | 21 | 48 | 0.4 | 48 |

| PHOSPHATASE ACTIVITY | Serogroup Y | | | |
|---|---|---|---|---|
| | Culture Phosphate | | Assay pH | |
| mg-polysaccharides | +plus | −minus | 5.0 | 7.0 |
| 0 hours | 0 | 0 | 0 | 0 |
| 3 hours | 2 | 8 | 0.5 | 8 |
| 8 hours | 3.7 | 25 | 0.2 | 25 |
| 12 hours | 8 | 43 | 0.13 | 43 |

| PHOSPHATASE ACTIVITY | Serogroup W-135 | | | |
|---|---|---|---|---|
| | Culture Phosphate | | Assay pH | |
| mg-polysaccharides | +plus | −minus | 5.0 | 7.0 |
| 0 hours | 0 | 0 | 0 | 0 |
| 3 hours | 1.7 | 7.2 | 0.5 | 7.2 |
| 8 hours | 2.4 | 41 | 0.18 | 41 |
| 12 hours | 6 | 47 | 0.1 | 47 |

Preparation of Meningococcal Meningitis Polysaccharide Vaccine:

Proteins and nucleic acid contaminants were precipitated with ethanol followed by polysaccharide precipitation with Cetavlon™, a polycationic compound used specifically to collect polyanionic polysaccharides. The residual contaminants were further removed by proteinase digestion and ultrafiltration. In this invention, we also used the polycationic compounds to specifically collect polyanionic polysaccharides after precipitating with Cetavlon™ which gave high purity vaccine polysaccharide components. Overnight, $CaCl_2$ was retained with Cetavlon™ precipitated polysaccharide at 4° C. The polysaccharides were further precipitated by slow addition of ethanol to collect polysaccharide residues and to remove contaminants in the preparation to give absolute purification of the vaccine compound. The phenol extraction step as described in another invention is totally removed and replaced with activated carbon filtration Activated carbon and Sephacryl gel filtration yielded high purity and quantity of polysaccharide vaccine components.

Polysaccharide Production in NMFM Medium

The *Neisseria meningitidis* serotypes were grown in separate 100-L bioreactors in NMFM medium for eighteen to twenty hours (as described earlier). Absorbance unit: Optical Density (OD) of bacterial growth of 10 at 600 nm, after a fermentation process of 12 hours, was chosen for the cultivation of polysaccharides from *N. meningitidis*. Formaldehyde (36.5–38%) 1% (v/v) was added to the bioreactors at 25 psi to kill the bacteria and then centrifuged (5,000×g for 30 min) to remove bacterial cells. The supernatant was collected, treated with 100% ethanol by slow addition with agitation and centrifuged to collect precipitate. The precipitate was re-dissolved in water and re-precipitated three times with ethanol by slowly adding 80% (v/v) ethanol, followed by centrifugation. The crude polymers were fractionated by stepwise precipitation with 1% hexa-decyl-tri-methyl-ammoniumbromide (Cetavlon™) at pH 7.0. at 4° C. overnight.

The precipitate was collected by centrifugation and re-suspended in water and 10% Cetavlon to a final concentration of 0.1% (w/v) was added and an equal amount of 0.9 molar $CaCl_2$ was then added to a final concentration of 1 mM and the solution left overnight with continuous mixing or agitation at 4° C. to remove endotoxin. The supernatant was collected by centrifuging at 9000 rpm. Cold ethanol was added to the supernatant to a final concentration of 25% and allowed to stand at 4° C. for 2 hours. The supernatant was collected by centrifuging at 5000 rpm for 40 min. Low molecular mass residual contaminants were removed with proteinase K digestion and filtered through activated carbon to remove trace organic compounds, repeatedly until $OD_{275}$ nm was <0.1. CPS was further purified by using the Sephacryl 200 gel filtration column using 50 mM ammonium formate elutions.

Polysaccharide Isolation and Characterization:

Total EPS was also analyzed by $^{13}C$ nuclear magnetic resonance (NMR) spectrometry. Samples were prepared by dissolving 8.8 mg of freeze-dried EPS from the Ion mutant and 13.8 mg of EPS from the wild-type strain in 0.7 ml of $D_2O$ (Cambridge Isotope Laboratories) and sonicating the samples for approximately 24 h. The spectra were collected with a Bruker DRX 500 spectrometer at 60° C. at a carbon frequency of 125.77 MHz with WALTZ-16 decoupling of the protons. For each, 60,000 transients of 32 k complex points were collected with a total recycle delay of 1.54 s. The data were processed by using an exponential window function with a line broadening factor of 2 Hz and then zero filled to a final size of 32 k real points.

The NMR data for structural classification of polysaccharides contain sialic acids and are in agreement with previously published data by Bhattacharjee, A. K., Jennings, H. J., and Kenny, C. P. (1974), Biochem. Biophys. Res. Commun. 61, 439; Bhattacharjee, A. K., Jennings, H. J., Kenny, C. P., Martin, A., and Smith, I. C. P. (1979, J. Biol. Chem. 250, 1926. Bhattacharjee, A. K., Jennings, H. J., Kenny, C. P., Martin, A., and Smith, I. C. P. (1976), Can. J. Biochem. 54, 1.

Electrophoresis of Polysaccharides

For electrophoretic analysis of cell surface-associated polysaccharides, cells were washed and extracted, followed by dialysis against distilled water. Samples were electrophoretically separated and stained. The samples were mixed with an equal volume of sample loading solution that contained 10% (vol/vol) glycerol, 0.25% (wt/vol) sodium deoxycholate (DOC), 0.125 M Tris (pH 6.8), and 0.0020% bromphenol blue. They were then electrophoresed through acrylamide gels which were comprised of a stacking phase that was 4% acrylamide polymerized in a buffer comprised of 0.5% (wt/vol) DOC and 0.125 M Tris-Cl (pH 6.8) and a resolving phase that was 18% acrylamide polymerized in a buffer containing 0.5% (wt/vol) DOC and 0.375 M Tris base (pH 8.8). The running buffer contained 0.290 M glycine, 0.037 M Tris base, and 0.250/0 (wt/vol) DOC. The gels were then stained for capsular polysaccharides. The stained polysaccharide patterns of each serotype showed class 1 to 3 bands that are agreeable to published data.

The purified polysaccharides produced from the above procedure using the medium NMFM were used in the human clinical trials in a multi-centered and double-blinded study in Niger and Burkina Faso in sub-Saharan Africa.

Animal and In-Vitro Study:

Briefly, animal studies conducted involving 24 healthy mice (12 Males and 12 females) of Balb/c 7-8 weeks old mice have demonstrated that the Meningococcal meningitis pure polysaccharides of serogorps A, C, Y & W-135 prepared usig NMFM medium are safe and non-toxic. The mice divided in to 4 groups of 6 mice per treatment. The first group was control animals. The second group immunized with 3.2 μg/ml, the third group with 6.5 μg/ml and the fourth group with 13 μg/ml of polysaccharides. Pre-immunized sera were collected at day zero and final sera were collected at 30-days after immunization. On Day 30, the mice were necropsied and histopathology was performed on each group. Prepared hematoxylin and eosin (H&E) stained slides of the following tissues, as available, were evaluated by Experimental Pathology Laboratories, Inc. (EPL®) for all submitted animals from both age groups: adrenals, brain, heart, kidneys, liver, lungs, lymph nodes, spleen, testes, thymus, and ovaries. No abnormal findings were observed from pathological data and none of the mice were dead during the study. There were no histomorphologic findings that could be definitively attributed to the test article vaccine exposure. In-vitro bactericidal assays has demonstrated that serogroups A, C, Y & W-135 elicited good immune response providing sero-conversion rates as measured by bactericidal antibody were: Sensitivity: Group A—81%, Group C—87%, Group Y —90% and Group W-135—82%; Specificity: Group A—86%, Group C —82%, Group Y—91% and Group W-135—93%. Statistical analysis of comparisons between pre and post immunization paired data was performed using the Wilcoxon test (one tailed). A P value of <0.05 was considered significant.

Human Trial and Analysis of Vaccine: NMVAC4-A/C/Y/W-135™

NmVac4-A/C/Y/W-135™ is a meningococcal polysaccharide vaccine comprised of and designed to confer protection against serogroups A, C, Y, and W-135 of the *Neisseria meningitidis* bacteria. This vaccine does not confer protection for any other serogroups. NmVac4 contains 50 μg of each purified capsular polysaccharide (200 μg total PS content) per dose. The polysaccharide is lyophilized and is designed for reconstitution using 0.5 mL sterile, pyrogen free water as a diluent. This vaccine is designed for subcutaneous administration, and must be used immediately after reconstitution. The vaccine is presented as a white pellet in a glass vial packaged together with a separate vial of clear, colorless, pyrogen-free water to be used as the diluent.

Five milliliter whole blood specimens were each drawn before vaccination (baseline, Week 0, or S-0) and at four additional milestone points as determined in the study protocol. In Burkina Faso, serum was drawn at S0, S+3 (three weeks post-vaccination ±5 days as stipulated in the trial protocol), S+8 (±5 days), S+24 (±5 days), and S+52 (±5 days). In Niger, serum samples were taken at S0, S+4 (±5 days as amended in the trial protocol), S+8 (±5 days), S+24 (±5 days), and S+52 (±5 days). Blood specimens were taken through 52 weeks to monitor the persistence of the immune response. Once drawn, all specimens were separated, and serum aliquots were maintained at −20° C. during shipping to and storage at the Diawara Biomedical Laboratory in Ouagadougou, Burkina Faso and the Tsoho Laboratory in Niamey, Niger for blinded serological testing.

Assay Techniques Used

The immunologic effects of the vaccine were studied using a commonly-utilized method of the enzyme-linked immunosorbant assay, or ELISA, and the use of a well-validated program obtained from the Centers for Disease Control for the determination of antibody concentration based on the data obtained from the optical densities recorded by the ELISA reader.

Enzyme-Linked Immunosorbant Assay

All available serum specimens were assayed using an enzyme-linked immunosorbant assay (ELISA) against the four meningococcal vaccine serogroups A, C, Y, and W-135 to assess the antibody primary immune response. Two-fold dilutions of test sera were prepared in sterile 96-well micro-titer plates to which were added serogroup-specific meningococcal antigens. For the screening of participants for enrollment into the study, global (all serogroups) ELISA optical densities were recorded. For the actual study, ELISAs of individual serogroups were performed.

Antigen coating was done by pipetting vaccine stock solution into the 96-well plate so that the final concentration was 1 μg/mL. The plate was then incubated at 4° C. overnight. The next day the plate was washed three times with PBS-Tween. After washing, 1% BSA-PBS was applied to each well and left at room temperature for approximately 1 hr. After 1 hr had elapsed, human serum was diluted and added or added directly and incubated at room temperature for two hours. HRP-conjugated anti-Human IgG antibody was then applied. The plate was again washed three times with PBS-Tween. The antibody was diluted in PBS-Tween and incubated at room temperature for 1 hr. TMB substrate was then added and the plate was washed three additional times with PBS-Tween. Additional TMB substrate was added and incubated for 5-30 min. A blue color appeared after approx. 1 min following addition of the substrate. The blue color intensified as a function of time. The reaction was stopped using an acid solution, and the color turned yellow. The ELISA plates for reaction were read at an Optical Density of 450 nm.

We have chosen ELISA bioassays for the trials because transportation problems of live bacteria from the United States to Africa for performing SBA bioassays. In addition, antigenic variation and human complement sensitivity of *Neisseria meningitidis* is a barrier to rely on SBA bioassays. It is therefore highly useful to have an ELISA to measure total serum antibody responses in a large number of vaccinated subjects. ELISA provided an accurate assessment of test vaccine immunogenicity. Used in this way, the ELISA is particularly useful for comparing (bridging) antibody responses to meningococcal vaccination for comparing different vaccines. The standard ELISA method for measuring serum antibodies to meningococcal serogroup-specific polysaccharides is both sensitive and reproducible.

Recently, a modified ELISA (used in this study) has been described which uses assay conditions primarily favoring the detection of higher-avidity anti-capsular antibodies.

IGG Anti-Meningococcal Antibody Determination

Using the process above provided, the optical densities had to be converted to antibody concentration to have any significance in this study. A program was obtained from the Centers for Disease Control (CDC) and the United States Department of Health and Human Services specifically for this purpose. The following information is available on the Internet at the website of Centers for Disease Control.

Division of Bacterial and Micotic Diseases:

ELISA for Windows® is a series of programs or program modules which process bioassay data collected from 96-well ELISA plates downloaded from several different models of ELISA readers. The program then performs a series of analyses on the processed data. This software is fully validated and the validation documents are available online.

An ELISA plate reader collects optical density measurements from each well and the operator imports these absorbance values to a desktop computer and stores the data as an ASCII text file. The ELISA program is able to abstract the standard series, individual serum samples, and quality control samples from this file. The standards data are used to form a characteristic or standard curve which may be modeled using a three point cubic spine or a four parameter logistic-log function. The four parameters of the logistic function may be estimated using two methods: iteratively re-weighted least squares and robust procedures. Estimation options include the Taylor series linearization (Gauss-Newton) and the Marquardt's compromise estimation algorithms. The standard curve is then used to interpolate antibody concentrations for the patient isolates and quality control samples. Summary statistics are calculated from these concentrations (means, standard deviations, coefficients of variation, etc). The program also forms plots of the standards data with the estimated standard curve superimposed on the data points.

Study Design

The study was a two-center study conducted in Burkina Faso and Niger. It is aimed to evaluate the efficacy, immunogenicity, and safety of a quadrivalent meningococcal vaccine in healthy subjects.

Primary Endpoint

The primary endpoint of the study was complete absence of symptoms or signs indicative of infection of meningococcal meningitis in volunteers injected with the vaccine.

Secondary Endpoint

The secondary endpoint was for the serological assays to confirm sufficient levels of antibody titers to indicate sero conversion for each serogroup (A, C, Y, W-135) of *Neisseria meningitidis*.

Adverse Events

All participants of this study were monitored for Adverse Events (AE) for the duration of the 52-week study. The ICH defines an Adverse Event as "any untoward medical occurrence in a patient or clinical investigation subject administered a pharmaceutical product and that does not necessarily have a causal relationship with this treatment. An AE can therefore be any unfavorable and unintended sign (including an abnormal laboratory finding), symptom, or disease temporally associated with the use of a medicinal (investigational) product, whether or not related to the medicinal (investigational) product." Severe Adverse Events (SAE) are described as "any untoward medical occurrence that at any dose: results in death, is life-threatening, requires inpatient hospitalization or prolongation of existing hospitalization, results in persistent or significant disability/incapacity, or is a congenital anomaly/birth defect."

Inclusion and Exclusion Criteria

This study was conducted in accordance to the standards of Good Clinical Practice (GCP) of World Health Organization (WHO), International Conference on Harmonisation (ICH), and the United States Food and Drug Administration (FDA). The criteria for inclusion and exclusion from the study are as follows:

Inclusion Criteria:

Healthy volunteers with acceptable serum antibody titers for *Neisseria meningitidis* and who had not received a meningitis vaccination in the past three years; Volunteers aged between 13 and 30 years. In the case of children under the age of 18 years, parental consent was obtained prior to recruitment in the study; both males and females were eligible; Patients who completed and signed their informed consent form.

Exclusion Criteria:

Less than 13 years or more than 30 years; Pregnancy or lactation; Clinically significant laboratory abnormalities including positive test for meningococcal infection; People with serious chronic diseases, such as cirrhosis of the liver, Hepatitis, and HIV/AIDS; Chronic medication use was evaluated on a case-by-case basis; Inability to understand all of the requirements of the study or to give informed consent and/or comply with all aspects of the evaluation; Use of immunosuppressive drugs such as systemic (but not topical or inhalant) steroids and cytotoxic agents; History of severe allergy; Serious pre-existing or concurrent chronic medical or psychiatric illnesses; Past history of significant head trauma, alcohol or substance abuse or other medical illnesses that might produce neurological deficit (such as cerebro-vascular disease); Use of systemic antibiotics in the previous month; Patients were excluded from this study if they were judged by the sub-Principal Investigators as having significant impairment in their capacity for judgment and reasoning that compromised their ability to make decisions in their best interest.

52-Week Study on Healthy Adults Aged 13-30

The study evaluated the Safety, Immunogenicity and Protective Efficacy of NmVac A, C, Y & W-135 meningococcal polysaccharide vaccine against Meningococcal infection in naive human volunteers for a period of 52 weeks. Blood was drawn at week 0 (prior to vaccination) and at four other milestone points at week 2, 8, 24 and 52.

Safety Profile: Immediate Reactions

Only mild local reactions were reported in the 30 minutes immediately following vaccination. Redness at the injection site was the most commonly reported AE for this time.

Local Reactions

Patients were given a set of cards to document their local reactions each day from day 0 to day 7. Incidence rates of solicited local reactions were low, with all being described as mild in nature. The most common local reaction was pain at the injection site. There were no AE reported as being either moderate or severe in nature. There were no unsolicited local reactions from day 8 to the conclusion of the trial.

Systemic Reactions

Incidence rates of solicited systemic reactions were also very low, with all symptoms being reported as being mild in nature. The most common symptom was mild fever, with a temperature less than 39.0° C. (102.2° F.). There were also isolated reports of mild headache, with a few subjects reporting both headache and mild fever. Again, there were no solicited systemic reactions reported as being moderate or severe in nature. There were no unsolicited systemic reactions from day 8 to the conclusion of the trial.

Immunogenicity of the Vaccine

Endpoint Evaluation

The primary endpoint for the evaluation of the efficacy of the vaccine was that no person injected with the vaccine would display symptoms or signs throughout the entire duration of the 52-week study consistent with being infected with meningococcal meningitis. Upon review of all information provided by the clinical trial staff, it has been confirmed that no person vaccinated contracted meningococcal disease.

The secondary endpoint was to show through serology data that a significant portion of the vaccinated population achieved sero-conversion, or had antibody levels sufficient enough to prevent infection of Neisseria meningitidis serogroups A, C, Y, and W-135. For our purposes, sero-conversion was determined as having an antibody concentration greater than or equal to two (2) micrograms per milliliter. The increase in optical density was also compared and showed the vaccine to be effective and persistent over the 52-week trial. However, since the most reliable and fully validated measure of vaccine efficacy is the concentration of antibodies present per milliliter of serum, this determination was the focus of this study.

The tables given below disclose the Number And Percent Of Participants Achieving The Minimum Protective Level (>2 µG/Ml). For Each Serogroup, with 95% cI, in Burkina Faso for weeks 3, 8, 24 and 52. In that (N) indicates number of participants with valid serology at stated interval; (n) indicates number of participants with antibody concentration >2 µg/ml; (%) indicates percentage of participants with antibody concentrations >2 µg/ml; (Cl) indicates confidence interval;

| Serogroup | n | % of n | 95% CI |
|---|---|---|---|
| Week 3 - Burkina Faso | | | |
| N = 147 | | | |
| A | 147 | 100.0 | 98.8, 100.0 |
| C | 147 | 100.0 | 95.7, 100.0 |
| Y | 147 | 100.0 | 98.3, 100.0 |
| W-135 | 147 | 100.0 | 98.6, 100.0 |
| Week 8 - Burkina Faso | | | |
| N = 125* | | | |
| A | 120 | 100.0 | 99.3, 100.0 |
| C | 125 | 100.0 | 96.4, 100.0 |
| Y | 125 | 100.0 | 99.1, 100.0 |
| W-135 | 125 | 100.0 | 99.1, 100.0 |
| Week 24 - Burkina Faso | | | |
| N = 124 | | | |
| A | 120 | 96.77 | 95.4, 98.1 |
| C | 124 | 100.0 | 94.3, 100.0 |
| Y | 124 | 100.0 | 98.0, 100.0 |
| W-135 | 124 | 100.0 | 98.3, 100.0 |

| Serogroup | n | % of n | 95% CI |
|---|---|---|---|
| -continued | | | |
| Week 52 - Burkina Faso | | | |
| N = 146 | | | |
| A | 143 | 98.0 | 96.9, 99.0 |
| C | 146 | 100.0 | 95.4, 100.0 |
| Y | 145 | 99.3 | 97.9, 100.0 |
| W-135 | 146 | 100.0 | 98.7, 100.0 |

*indicates for Week 8 Serogroup A, N = 120.

In Burkina Faso, 100% of the subjects showed sero-conversion through weeks 3 and 8. For week 24, nearly 97% of serogroup A showed sero-conversion, while the other three serogroups all maintained 100% sero-conversion. For Week 52, serogroup A showed 98% of the subjects achieved sero-conversion, 99% for serogroup C, and 100% for the remaining two serogroups.

The results for Niger were slightly different, with only 57% of subjects achieving sero-conversion for serogroup A through the first four weeks. The other serogroups at week 4 were all between 96 and 99 percent sero-converters. For week 8 in Niger, 80% of serogroup A demonstrated sero-conversion, and the other serogroups were all at 99-100%. For weeks 24 and 52 in Niger, all subjects demonstrated sero-conversion.

The results of this trial showed the meningococcal vaccine to be safe and well-tolerated in all study participants. There was a low incidence of any adverse effect, and all were categorized as being mild in nature. There were no severe reactions to the vaccine. The immunogenicity of the vaccine also proved excellent, as antibody concentrations rose substantially in most vaccinated subjects. This rise in nearly all cases was significant enough to confer protection against infection.

Generation of Low-Molecular-Weight Polysaccharides for the Purpose of Conjugation to Carrier Protein (Diphtheria Toxoid or Tetanus Toxoid):

The CPS were acidified, dialyzed, and evaporated to a small volume and the resulting polymers were precipitated with excess ethanol, and then isolated and were submitted to both analytical and chemical methods. Total carbohydrate content was determined by the phenol sulfuric acid assay. Total protein content was determined according to Lowry et al. (1951), and phosphate content by the procedure recommended by Ames (1966). Determination of polysaccharide composition; A, C, Y and W-135 were hydrolyzed with 0.5M sulfuric acid for 18 hr at 100° C. and the resulting polysaccharides were examined as their alditol acetates by gas liquid chromatography-mass spectrometry (GC-MS).

Colorimetric analysis of different Neisseria meningitidis serotypes showed purified polysaccharide content (mg/L) produced by each serotype of Neisseria meningitidis at 12 hours: A=43.0; C=48.0; Y=43.0 and W-135=47.0 per liter. In this invention, the purified polysaccharides collected from crude polysaccharide preparations were at more than 50% for each Neisseria meningitidis serotype. The CPS purity indicates that the invented procedure can yield maximum quantity.

Concentrated supernatants containing ethanol-soluble, extracellular low-molecular-weight polysaccharides were concentrated under vacuum. Samples were applied to a Sephadex G-25 column (1 by 52 cm) which was eluted at room temperature with 0.15 M ammonium acetate (pH 7.0) containing 7% propanol (vol/vol) at a rate of 15 ml/h. Fractions (1 ml) were collected and assayed for carbohydrate content. Material was pooled, concentrated, and subsequently desalted using a Sephadex G-15 column (1 by 49 cm). The Sephadex G-15 column was eluted at room temperature with 7% propanol (vol/vol) at a rate of 15 ml/h. Fractions (1 ml) were collected and assayed for carbohydrate content. Material was pooled and subsequently analyzed by thin-layer chromatography (TLC) using aluminum-backed Silica Gel 60 plates and a butanol-ethanol-water (5:5:4) solvent system. Samples were visualized on TLC plates by charring at 170° C. for 20 min after spraying with 5% sulfuric acid in methanol (vol/vol).

Sonication Technique:

A Heat-Systems with an ultrasonic probe/sonotrode LS24d5 for UIS250L was used as the continuous source of power for the generation of the micro-polysaccharides. Serial dilutions of sonicated albumin microspheres of known concentrations based on Coulter counter analysis were used to determine the laser particle concentration measurements.

The half-inch titanium probe from a sonicator was placed beneath the surface of the polysaccharide solution contained in a plastic bottle surrounded by ice cubes. With the tip of the probe held firmly, the sonicator was turned on. After 30 seconds the probe was lowered enough to permit the tip of the sonicator to briefly contact the surface of the liquid, thus permitting a period of surface agitation. Once the surface agitation occurred, the tip of the sonicator was lowered beneath the surface of the liquid for 5 minutes. The surface agitation process was briefly performed a second time for 5 minutes.

Laser Sampling Technique:

Before each test, background counts of particles of polysaccharides were performed. Three separate determinations were recorded by the laser counter. With a predetermined threshold correlation chart provided by the manufacturer, the background counts were considered acceptable if the absolute counts did not exceed 200 counts/ml$^3$. The Soectrex Fourier analysis was not limited by the threshold values, thus the frequency analysis included the distribution of all background counts. Immediately after the sonication process was completed, 1 ml of the sonicated solution was analyzed.

Laser Analysis:

A scanning laser particle counter (Spectrex Corporation, Redwood City, Calif.) was used to determine the in vitro diameters and concentrations of the micro-polysaccharides. As the laser beam passed through the solution that contained the micro-polysaccharides, a pre-designed "sensitive zone" at the center of the container served as the sampling site for the examination. When the laser beam struck a polysaccharide, there was near-angle scatter of deflected light. The magnitude of the laser deflection was directly proportional to the diameter of the polysaccharide. Following a 25-second counting period, the concentration of the polysaccharide per cubic centimeter was displayed on an electronic readout.

In conjunction with the laser analysis of the absolute particle counts, a Fourier transform of the laser pulse amplitudes measured the diameters of the polysaccharide within the sensitive zone. After a 10 minute sampling period, a frequency histogram for the sample was generated. The absolute numbers of the polysaccharides found in each size channel were calculated by multiplying the percentages listed in the frequency histogram by the absolute counts determined from the laser scanner.

The contents of the beaker were then scanned with the laser counter to determine the in situ diameters and concentration of the sonicated micro-polysaccharides. The laser counter provided the absolute concentrations within the 1 $ml^3$ region of analysis, and the Fourier analysis listed the polysaccharide diameter frequency of occurrence within a sampled time period. An example of the frequency histogram is shown in FIG. 17. Background particulate counts obtained before the analysis were subtracted to obtain the actual concentration of the sonicated micro-polysaccharides. In effect, the background particulate contamination was small (less than 10%) relative to the large numbers of polysaccharides measured during the analysis.

Calibration Studies:

Particle size diameters were assessed with manufactured solid latex spheres. The size distribution was described as 0.03±0.02 μm. Coulter counter determinations of serial dilutions were used to check the concentrations recorded from the laser counter. The micro-polysaccharide size distributions obtained were similar. These distributions were modeled to quantify any differences between particle size, and it was concluded that any differences were negligible, since similarly shaped distributions would be clinically applicable. Thus the method is reproducible.

This study describes the results of developing and analyzing the sonication method for generating micro-polysaccharides. The reproducibility of the sonication technique was demonstrated for the production of micro-polysaccharides. This technique promises to provide a rapid, economical, and safe method when compared with chemical depolymerization prior to conjugation with a carrier protein. Chemical and enzymatic methods are available for the specific degradation of polysaccharides for conjugation to carrier proteins and include hydrolyses with acid, alkali, or glycanase-mediated, oxidations, and eliminations with alkali- or lyase-mediated β-elimination, which can create chemical contaminants in the vaccine preparation and require analysis and purification.

Low Molecular Weight Extra-Cellular Polysaccharides

To monitor the purification of low molecular weight EPS from *Neisseria meningitidis* cultures, TLC is performed. When the low-molecular-weight, extra-cellular polysaccharides of *N. meningitidis* mutants were examined by TLC, a major spot, migrating with a substantially higher molecular weight EPS was detected. Indeed, this material was a major contaminant within higher molecular weight EPS preparations and represented approximately 75% of the total carbohydrate present within the low-molecular-weight fraction isolated from culture supernatants of *N. meningitidis* mutants. Further analysis revealed that this contaminant could be bound to DEAE-cellulose at pH 8.4 and subsequently eluted using a buffer containing 200 mM KCl, indicative of anionic character.

Characterization of the extra-cellular anionic contaminant material isolated from mutants was performed using negative ion fast atom bombardment mass spectrometry (FABMS).

Analysis:

Fast atom bombardment mass spectrometry analysis revealed a mass spectrum distinctly different from that obtained for the EPS. When the anionic, low-molecular-weight extra-cellular polysaccharide material obtained from mutants was examined by negative ion FABMS, the analysis revealed a very different spectrum, although the predominant molecular ion species had m/z values in the same range as the EPS. This result confirmed that the anionic low-molecular-weight polysaccharide material is very similar in size to the EPS, consistent with the fact that these materials co-purify on Sephadex G-25.

Compositional analysis of the extra-cellular low-molecular-weight polysaccharide isolated from the *N. meningitidis* mutants was performed using gas chromatography linked to electron impact mass spectrometry. This is the same composition previously reported for the high molecular weight exo-polysaccharide of *N. meningitidis* strains.

Structural examination of the putative low molecular weight EPS was performed using methylation and gas chromatography-mass spectrometry analysis, as well as 1-D $^1$H nuclear magnetic resonance (NMR) analysis. The NMR spectra previously published for high-molecular-weight EPS of *N. meningitidis* strains is in good agreement with our spectrum.

Result

Based on FABMS and compositional analysis results, additional analyses were performed on the low-molecular-weight anionic polysaccharide material obtained from culture supernatants of the wild-type parent strains. These results reveal that both mutant and the wild-type parent strains produce and excrete a low-molecular-weight form of EPS.

Based on the gel permeation chromatography and negative ion FABMS, it may be concluded that this material corresponds to a dimeric form of the pentasaccharide repeating unit of the *N. meningitidis* EPS. Compositional analysis concludes that both mutant and the wild-type parent strains produce and excrete a low-molecular-weight form of EPS.

Production and Purification of Diphtheria Toxoid:

The crude toxoid is isolated from the detoxified filtrate of the culture of the Toronto Park 8 strain of Corynebacterium diphtheriae. It was grown in Mueller-Hinton liquid medium without peptone with the addition of casein hydrolysate base in a 100 Liter fermentor with a working volume of 50 for 60 hours, at which time the pH is adjusted to 7.0. The culture was inactivated with formaldehyde (37%) to convert diphtheria toxin to diphtheria toxoid. The purification, as presently carried out, consists of a simple three step salt fractionation of the proteins of the crude toxoid, accomplished at room temperature, at pH of 6.0 imparted by strong solutions of ammonium sulfate, and at a regulated concentration of total protein.

For purposes of the first precipitation, the protein content of crude toxoid preparations is 20 grams per liter. The entire protein content of the crude toxoid is salted out by adding solid ammonium sulfate to 50 percent saturation at pH 4.0. The precipitate is collected by filtration using 0.2 μm filter giving a protein concentration of about 16 grams per liter. This solution is brought to 35 percent saturation with ammonium sulfate by adding the appropriate volume of the 1× Phosphate buffered saline. The suspension is allowed to stand at least 30 minutes and is then filtered. The clear filtrate is brought to 50 percent saturation using saturated salt. After flocculating, this precipitate is collected by filtration and dissolved in a minimal volume of water. The solution is dialyzed free of sulfate in cold distilled water overnight at 4° C. The concentrate of purified toxoid is made and filtered by aseptically adding two equal volumes of diluting saline and is put through the filter.

Purity Analysis

Purity of Diphtheria toxoid is determined as units per mg protein and compared to the value for a commercially available purified and certified Diphtheria toxoid (Sigma-Aldrich) by a method where Lf units per mg protein nitrogen was compared with the value of pure toxoid (2170 Lf per mg). Percent of purity is based on Trichloroacetic acid precipitated nitrogen (81) and total nitrogen minus ammonium sulfate nitrogen (40%) given 95% purity, where 5% remaining impurity belongs to non-toxic proteins and toxoid yield Lf=26%.

The purified toxoid is stored in this form until it is to be prepared for clinical trials in mice.

Conjugation of Polysaccharides to Diphtheria Toxoid:

*Neisseria meningitidis* capsular polysaccharides are poor immunogens particularly in young infants. However, conjugation of bacterial polysaccharides to immunogenic carrier proteins generally result in conjugates that induce strong anti-polysaccharide T-helper-cell dependent immune responses in young infants. The magnitude of the response and the extent of the T-helper-cell dependency is related to the chemical characteristics of the particular conjugate such as presence or absence of polysaccharide-protein cross-linking, presence or absence of spacer arms, character of spacer arms, type of carrier protein, size of conjugated polysaccharide hapten, and molar degree of substitution. In the present study, no new method for the preparation of polysaccharide-protein conjugates is presented. However, in this invention, standard procedures were used to produce non-chemically depolymerized polysaccharides by means of sonication to micro-polysaccharides of (5100 to 9900 Daltons) before coupling with purified Diphtheria toxoid or Tetanus toxoid by reductive amination, as previously described by other workers referred to below. This conjugated vaccine protects humans of all ages including children below the age group of 2 years against *N. Meningitidis* sero groups A, C, Y and W-135.

Preparation of *Neisseria meningitis* polysaccharides and Diphtheria toxoid (DT) or tetanus toxoid (TT) carrier protein conjugates. Meningococcal serogroup A, C, W-135, and Y polysaccharides and DT or CRM197-based conjugates were prepared as already described (Costantino, P., F. Norelli, A. Giannozzi, S. D'Ascenzi, A. Bartoloni, S. Kaur, D. Tang, R. Seid, S. Viti, R. Paffetti, M. Bigio, C. Pennatini, G. Averani, V. Guarnieri, E. Gallo, N. Ravenscroft, C. Lazzeroni, R. Rappuoli, and C. Ceccarini. 1999. Size fractionation of bacterial capsular polysaccharides for their use in conjugate vaccines. Vaccine 17:1251-1263.; Costantino, P., S. Viti, A. Podda, M. A. Velmonte, L. Nencioni, and R. Rappuoli. 1992. Development and phase 1 clinical testing of a conjugate vaccine against meningococcus A and C. Vaccine 10:691-698.; Ravenscroft, N., G. Averani, A. Bartoloni, S. Berti, M. Bigio, V. Carinci, P. Costantino, S. D'Ascenzi, A. Giannozzi, F. Norelli, C. Pennatini, D. Proietti, C. Ceccarini, and P. Cescutti. 1999. Size determination of bacterial capsular oligosaccharides used to prepare conjugate vaccines. Vaccine 17:2802-2816.).

The same conjugation chemistry was used for the preparation of Y constructs. The polysaccharide content of serogroups C, W-135, and Y conjugates was quantified by sialic acid determination, Serogroup A conjugate was quantified by mannosamine-1-phosphate chromatographic determination. The protein content was measured by a micro-bicinchoninic acid assay of Lowry et al. (1951). The polysaccharide-to-protein ratio of conjugates ranged between 0.3 and 1.5, similar to that of cross-reacting material DT and CRM-based conjugates.

Safety and Immunogenicity of Quadrivalent Meningococcal Vaccine Materials and Methods The quadrivalent meningococcal vaccine is being studied for its ability to elicit an immune response significant enough to sustain a protective level within the individual vaccinated. All clinical trial protocols were evaluated and approved by an Animal Institutional Review Board and Independent Ethics Committee of Maryland. The animal trials were conducted at Spring Valley Laboratories, Maryland.

Animal Clinical Trial Protocol to Test Meningococcal Meningitis A, C, Y. AND W-135 Polysaccharide Vaccine Conjugated with Diphtheria Report Formulation:

Meningococcal meningitis A/C/Y/W-135 conjugated to Diphtheria Toxoid vaccine is manufactured as a sterile, clear to slightly turbid liquid and is formulated in sodium phosphate buffered isotonic sodium chloride solution to contain 4 μg each of meningococcal A, C, Y, and W-135 polysaccharides conjugated to approximately 48 μg of diphtheria toxoid protein carrier.

Experimental Design

The purpose of this study was to investigate the sub-acute toxicity of Meningococcal meningitis A, C, Y, and W-135 polysaccharide vaccine conjugated with Diphtheria Toxoid following multiple exposures (two doses) for a period of 30 days. Forty neonatal mice (14 days old at the start of the study) and forty 6-8 week old Balb/c mice were each divided into four groups of five males and five females per group. The 14-day age group was dosed at 0.1, 0.2, and 0.4 μg and the 6-8 week age group was dosed at 0.2, 0.4, and 0.8 μg. Additional mice were used to provide adequate samples for baseline clinical and serological assays. All non-baseline mice received intramuscular injections on Day 0 and Day 14. The other group (control) received saline. On Day 30, the mice were necropsied and histopathology was performed on two mice from each group, one male and one female. Prepared hematoxylin and eosin (H&E) stained slides of the following tissues, as available, were evaluated by Experimental Pathology Laboratories, Inc. (EPL®) for all submitted animals from both age groups: adrenals, brain, heart, kidneys, liver, lungs, lymph nodes, spleen, testes, thymus, and ovaries. All microscopic alterations observed were represented in the Histopathology Incidence Tables. The findings were graded from 1-5 depending upon severity or were indicated as not remarkable (X) or not present (N). Additionally, non-required tissues were occasionally found sectioned with the required tissues and were also listed on the Histopathology Incidence Tables with appropriate designations as described above.

Results

In the 14-day age group, a few minimal findings were observed in heart, kidney, liver, or spleen. These findings ranged from mineralization (heart and kidney) to small inflammatory foci (liver) and one incidence of increased extramedullary hematopoiesis in the spleen (one Group 7 female). Most of these changes were considered to be incidental background findings common to this strain of mouse. Mineralization in the heart is also common in the Balb/c mouse strain but is usually epicardial rather than the random myocardial foci observed in these mice. In the 6-8 week age group, there were similar findings as observed in the 14-day age group with additional changes seen in the adrenal gland (one incidence of subcapsular hyperplasia in a Group 2 female), chronic active inflammation along the pelvis of the kidney (one Group 2 female), mononuclear cell infiltration (one Group 3 male) and a tubular cyst (one Group 4 female) in the kidney, and focal necrosis in the liver (one Group 3 male). Most of these changes in the 6-8 week age group were minimal although the chronic active inflammation in the kidney pelvis and chronic inflammation in the liver of one Group 2 female and chronic inflammation and focal necrosis in the liver of one Group 3 male were at a slight/mild severity. As for the 14-day age group, all of these changes may be incidental background findings. During the course, one neonatal mice died form some unknown physical etiology. Neither on autopsy nor on histology there were any findings that would lead to the etiology.

In summary, with only one animal per group to evaluate, differences in incidence of common background findings were not apparent. There were no histomorphologic findings that could be definitively attributed to the test article vaccine exposure.

Immunological Studies:

Serum Samples:

We analyzed 160 serum samples (80 serum samples assigned to day Zero and 80 serum samples assigned to day thirty) for determination of serum antibodies against *Neisseria meningitidis* subgroups A, C, Y, and W-135. 24 serum samples were designated as un-vaccinated mice of day 0 and day 30.

Objectives:

In the present study, we determined whether *Neisseria meningitidis* subtypes A, C, Y, W-135 polysaccharide diphtheria conjugate antigens are able to induce humoral immune response as shown by in vitro bactericidal assay. In this study, we report the results of analysis of the bactericidal responses to meningococcal serogroups A, C, Y, and W-135 strains in sera from vaccinated mice as in comparison with un-vaccinated mice measured by the standardized bactericidal Goldschneider assay (Maslanka et al 1997) (for A, C, Y, W-135 polysaccharide vaccine). ELISA for anti-meningitis A,C,Y, W-135 antibody levels against each serotype was determined by an ELISA protocol described by Granoff, et al 1998. Statistical analysis of comparisons between pre - and post-immunization paired data was performed using the Wilcoxon test (one tailed). A P value of <0.05 was considered significant.

Bactericidal Assays:

The test sera were heat inactivated (56° C. for 30 min) to remove intrinsic complement activity. Aliquots of sera were screened for anti-serogroup of *Neisseria meningitidis* subgroups A, C, Y, W-135 antibodies by enzyme-linked immunosorbent assay (ELISA). Sera that were negative by ELISA were screened for the presence of bactericidal activity. Test sera were assayed for bactericidal activity at a 1:2 starting dilution using all the *Neisseria meningitidis* subgroups A, C, Y, W-135 standard bacteria received from the Centers for Disease Control (CDC). To perform the standardized assay, the test organisms were grown on blood agar and were re-suspended in Gey's buffered salt solution containing 0.5% bovine serum albumin. Bacterial killing in the final reaction vial was measured after 60 min of incubation at 37° C. Bactericidal titers were defined as the highest serum dilution giving a 50% decrease in colony-forming units (CFU) compared to the CFU measured at time zero. The test organisms for the Goldschneider assay were grown for 5 hours on Mueller-Hinton chocolate agar and re-suspended in Dulbecco's phosphate-buffered saline. Bacterial survival in the final reaction mixture was measured after 30 minutes of incubation at 37° C. The bactericidal titer was calculated from the following equation: Percent survival=(CFU of sample well at 30 min/CFU with the complement control at 0 min)×100. The bactericidal titer assigned was the 50% intercept when percent survival.

Results

Humoral Immune Response:

From the Bulb/c mice immunization experiment, the geometric means of antibody concentrations specific to meningitis serogroups A, C, Y, W-135 diphtheria conjugate vaccine after immunization were measured in serum bactericidal assays. The specificity and sensitivity to each serogroup were determined by ELISA. From the Bulb/c mice immunization experiment, the geometric means of antibody concentrations specific to meningitis serogroups A, C, Y, W-135 diphtheria conjugate vaccine after immunization were measured. are shown in Table 10. Significant differences in antibody concentrations between pre-and post-immunization samples were observed for each serotype studied. Non-immunized controls showed no increase in antibody concentrations. All serotypes resulted in significant antibody production and humoral response in mice. This combination of A, C, Y, and W-135 polysaccharides generated significant bactericidal titers against all four *N. meningitidis* serogroups and showed increased antibody levels as a result of vaccination with the meningococcal A,C,Y,W-135 diphtheria conjugate vaccine. The bactericidal activity in serum from control mice was insignificant.

Cell Mediated Immune Response

A lymphocyte proliferation assay was performed according to the method described by us in our journal article (Reddy J R, Kwang J, Varthakavi V, Lechtenberg K F, Minocha H C. Semiliki forest virus vector carrying the bovine viral diarrhea virus NS3 (p80) cDNA induced immune responses in mice and expressed BVDV protein in mammalian cells. Comp. Immunol. Microbiol. Infect. Dis. 1999 October; 22(4):231-46). Spleen cell and T-cell proliferation responses to meningococcal serotypes A,C,Y,W-135 conjugated to DT immunized mice had the mean significance difference (p=<0.01) from those of the control mice. A higher degree of antigen-induced proliferation occurred in spleen cells from mice immunized with as low as 0.1 µg in neonatal mice and 0.2 µg in 6-8 week old mice.

Bactericidal antibody response in serum from meningococcal A, C, Y, W-135 Polysaccharides; Geometric Mean titer (95%) A, C, Y, W-135 diphtheria conjugate vaccine for immunized Mice is 1: 256; and Geometric Mean titer (95% ACYW-135 diphtheria vaccine for control Mice is <1:2.

summary of bactericidal antibody response in serum from Meningococcal ACYW-135 polysaccharides; Geometric mean titer (95%) ACYW-135 diphtheria conjugate vaccine for immunized mice (6-8 week) is 1: 512; and Geometric mean titer (95%) ACYW-135 diphtheria conjugate vaccine for control immunized mice (6-8 week) is <1:4

The following summarizes the distribution of the bactericidal titers measured by Goldschneider assay. Post-vaccination sera: Meningococcal A, C, Y, W-135 diphtheria conjugate vaccine had titers of 1:256 or greater with (P<0.001). Thus, mice vaccinated with Meningococcal—A, C, Y, W-135 capsular polysaccharides diphtheria conjugate vaccine and have bactericidal antibodies against Meningococcal meningitis compared to unvaccinated mice.

Analysis of Specificity and Sensitivity if the Standardized Assay Measured on Meningococcal—A, C, Y, W-135 Diphtheria Conjugate Vaccination.

The relationship between the bactericidal titers measured by the subtype A, C, Y, W-135 sera and control sera assays for increased antibody levels resulted in higher bactericidal titers against all serogroups of meningitis bacteria measured by ELISA.

Sensitivity and specificity of Meningitis serogroup A,C,Y, W-135 antibodies; For Serogroup A, sensitivity (%)—91 and specificity (%)—86; Serogroup C sensitivity (%)—87 and specificity (%)—82; Serogroup Y, sensitivity (%)—86 and specificity (%)—85; Serogroup W-135, sensitivity (%)—82 and specificity (%)—93.

It can be easily understood by persons of ordinary skill in the art that the NMFM Medium (*Neisseria Meningitidis* Fastidious Medium) can have several other possible combinations of the ingredients of the medium and the embodiment of the NMFM medium described herein is limited only by the claims made herein.

The invention claimed is:

1. A *Neisseria meningitidis* fastidious culture medium (NMFM) for producing capsular polysaccharides from *Neisseria meningitidis* comprising: DI (deionizer) water, NaCl, $K_2SO_4$, KCl, trisodium citrate.$2H_2O$, $MgSO_4.7H_2O$, $MnSO_4.H_2O$, $MnCl_2.6H_2O$, vitamin B12, NAD (Nicotinamide Adenine Dinucleotide) thiamine HCl, soy peptone, D-glucose, L-glutamic acid, L-arginine, L-serine, L-cysteine, glycine, morpholinepropanesulphonic acid [MOPS], $CaCO_3$ to maintain pH at 6.5 to 7.0 and $Fe_2(SO_4)_3$ for serogroup A and $NH_4Cl$ for serogroup W-135.

2. The culture medium according to claim 1, a liter comprising: 900mL of DI (deionized) water, NaCl - 0.35 g, $K_2SO_4$-0.20 g, KCl - 0.20 g, trisodium citrate.$2H_2O$ - 0.70 g, $MgSO_4.7H_2O$ - 0.60 g, $MnSO_4.H_2O$ - 1.00 mg, $MnCl_2.6H_2$ O - 40 mg, vitamin B12 (source *Saccharomyces cerevisiae*)-10.0 g, NAD (Nicotinamide Adenine Dinucleotide) thiamine HCl - 0.25 g, soy peptone -15 g, D-glucose -10 g, with concentrations of L-glutamic acid - 5.10 mM, L-arginine -0.237 mM, L-serine - 0.476 mM, L-cysteine - 0.254 mM, glycine -1.998 mM, morpholinepropanesulphonic acid (MOPS) - 10.0 mM, CaCO3-0.25 mM to maintain pH at 6.5 to 7.0, (Fe2 $(SO_4)_3$-0.5g for serogroup A and $NH_4Cl$- 1.25 g for serogroup W-135.

3. The culture medium according to claim 1, wherein the vitamin B12 is from a yeast source.

4. The culture medium according to claim 3, wherein the yeast source is *Saccharomyces cerevisiae.*

5. A method of producing a meningococcal meningitis vaccine comprising capsular polysaccharides, the method comprising the steps of:

1. culturing *Neisseria meningitidis* to produce capsular polysaccharides of serotypes A, C, Y and W-135, in the *Neisseria meningitidis* fastidious medium (NMFM) of claim 1;
2. precipitating and isolating the capsular polysaccharides from the culture;
3. purifying the capsular polysaccharides of any residual cellular biomass; and
4. depolymerizing the capsular polysaccharides mechanically.

6. The method according to claim 5, comprising producing the maximum amount of capsular polysaccharides with minimal amount of cellular biomass and endotoxins in the minimum amount of time by restricting the fermentation process to about 12 hours.

7. The method according to claim 5, comprising precipitating polyanionic capsular polysaccharides using a polycationic compound to specifically collect the polyanionic capsular polysaccharides by precipitating slowly with the polycationic compound giving high purity and enhanced production of capsular polysaccharides.

8. The method according to claim 5, comprising purifying and increasing the rate of production of the capsular polysaccharides from the polysaccharide precipitate by slowly adding polycationic compound and calcium chloride to the polysaccharide precipitate.

9. The method according to claim 5, wherein mechanical depolymerization of the capsular polysaccharides is carried out using sonication.

10. The method according to claim 5 comprising, producing the meningococcal meningitis vaccine without any endotoxin.

11. The method according to claim 5, further comprising the step of conjugating the depolymerized capsular polysaccharide to one or more carrier proteins.

12. The method according to claim 11, wherein the depolymerized polysaccharides have an average molecular weight of 5100 to 9900 Daltons.

13. The method according to claim 11, wherein the carrier protein is diphtheria toxoid.

14. The method according to claim 11, wherein the carrier protein is tetanus toxoid.

15. The method according to claim 5, wherein the calcium carbonate concentration of the NMFM medium is 0.001 percent per liter of the NMFM medium which maintains the pH of the medium between 6.5 to 7.0.

16. The method according to claim 5, wherein the organic phosphate concentration of the NMFM media is 0.40 percent per liter which reduces the production of cellular biomass and increases the production of capsular polysaccharides.

17. The method according to claim 5, comprising reducing the availability of oxygen for consumption thereby increasing the yield of *Neisseria meningitidis* serogroups A, C, Y, and W-135 capsular polysaccharides.

18. The method according to claim 17, wherein the specific rate of endotoxin production is reduced.

* * * * *